US012678553B2

(12) United States Patent
Laitenberger et al.

(10) Patent No.: US 12,678,553 B2
(45) Date of Patent: Jul. 14, 2026

(54) TEMPERATURE MONITORING AND CONTROL FOR NEGATIVE PRESSURE WOUND THERAPY SYSTEMS

(71) Applicant: T.J.Smith and Nephew, Limited, Hull (GB)

(72) Inventors: Peter Georg Laitenberger, Cambridge (GB); Jamie Owst, Hull (GB); Felix Clarence Quintanar, Hull (GB); Neil Andrew Ramsbottom, Bolton (GB); Roberto Damiao Da Costa Rodrigues, Hull (GB)

(73) Assignee: T.J.Smith and Nephew, Limited, Hull (GB)

( * ) Notice: Subject to any disclaimer, the term of this patent is extended or adjusted under 35 U.S.C. 154(b) by 410 days.

(21) Appl. No.: 18/020,240

(22) PCT Filed: Sep. 22, 2021

(86) PCT No.: PCT/EP2021/076022
§ 371 (c)(1),
(2) Date: Feb. 7, 2023

(87) PCT Pub. No.: WO2022/073762
PCT Pub. Date: Apr. 14, 2022

(65) Prior Publication Data
US 2024/0024565 A1 Jan. 25, 2024

(30) Foreign Application Priority Data

Oct. 5, 2020 (GB) ........................................ 2015747
Apr. 7, 2021 (GB) ...................................... 2104922

(51) Int. Cl.
*A61M 1/00* (2006.01)

(52) U.S. Cl.
CPC ..... *A61M 1/962* (2021.05); *A61M 2205/3331* (2013.01); *A61M 2205/3368* (2013.01)

(58) Field of Classification Search
CPC .......... A61M 1/00; A61M 1/70; A61M 1/962; A61M 2205/3368; A61M 1/80;
(Continued)

(56) References Cited

U.S. PATENT DOCUMENTS 3,874,387 A 4/1975 Barbieri
4,224,941 A 9/1980 Stivala
(Continued)

FOREIGN PATENT DOCUMENTS

CN 201664463 U 12/2010
CN 201910614 U 7/2011
(Continued)

OTHER PUBLICATIONS

International Search Report and Written Opinion for Application No. PCT/EP2021/076022, mailed on Dec. 21, 2021, 13 pages.
(Continued)

*Primary Examiner* — Philip R Wiest
*Assistant Examiner* — Meagan Ngo
(74) *Attorney, Agent, or Firm* — Knobbe, Martens, Olson & Bear, LLP

(57) ABSTRACT

A negative pressure wound therapy can include a negative pressure source configured to provide negative pressure to a wound of a patient covered by a wound dressing, first sensor and second sensors configured to measure temperature of the negative pressure system, electronic control circuitry configured to control operation of the negative pressure source responsive to temperature measured by the first sensor, and a programmable controller configured to control operation of the negative pressure source responsive to temperature measured by the second sensor, the controller configured to
(Continued)

control operation of the negative pressure source independently of the electronic control circuitry.

21 Claims, 17 Drawing Sheets

(58) Field of Classification Search
CPC .......... A61M 2205/85; A61M 2230/50; A61M
1/918; A61M 1/90; A61M 1/96; A61M
2005/3561; A61M 11/962; A61M 1/701;
A61F 13/05; G16H 40/63
See application file for complete search history.

(56) References Cited

U.S. PATENT DOCUMENTS

| | | | |
|---|---|---|---|
| 4,398,910 A | 8/1983 | Blake et al. |
| 4,534,356 A | 8/1985 | Papadakis |
| 4,569,674 A | 2/1986 | Phillips et al. |
| 4,624,656 A | 11/1986 | Clark et al. |
| 4,681,562 A | 7/1987 | Beck et al. |
| 4,767,943 A | 8/1988 | Adler et al. |
| 4,979,944 A | 12/1990 | Luzsicza |
| 5,055,195 A | 10/1991 | Trasch et al. |
| 5,055,198 A | 10/1991 | Shettigar |
| 5,056,510 A | 10/1991 | Gilman |
| 5,152,757 A | 10/1992 | Eriksson |
| 5,181,905 A | 1/1993 | Flam |
| 5,266,928 A | 11/1993 | Johnson |
| D357,743 S | 4/1995 | Bilitz et al. |
| 5,527,293 A | 6/1996 | Zamierowski |
| 5,549,584 A | 8/1996 | Gross |
| 5,643,189 A | 7/1997 | Masini |
| 5,779,657 A | 7/1998 | Daneshvar |
| 5,833,646 A | 11/1998 | Masini |
| 5,902,256 A | 5/1999 | Benaron |
| 5,964,723 A | 10/1999 | Augustine |
| 6,071,267 A | 6/2000 | Zamierowski |
| 6,142,982 A | 11/2000 | Hunt et al. |
| 6,168,800 B1 | 1/2001 | Dobos et al. |
| 6,183,438 B1 | 2/2001 | Berguer |
| 6,225,523 B1 | 5/2001 | Masini |
| 6,261,276 B1 | 7/2001 | Reitsma |
| 6,261,283 B1 | 7/2001 | Morgan et al. |
| 6,398,767 B1 | 6/2002 | Fleischmann |
| 6,458,109 B1 | 10/2002 | Henley et al. |
| 6,471,982 B1 | 10/2002 | Lydon et al. |
| 6,599,262 B1 | 7/2003 | Masini |
| 6,607,495 B1 | 8/2003 | Skalak et al. |
| 6,685,681 B2 | 2/2004 | Lockwood et al. |
| 6,787,682 B2 | 9/2004 | Gilman |
| 6,794,554 B2 | 9/2004 | Sessions et al. |
| 6,800,074 B2 | 10/2004 | Henley et al. |
| 6,855,135 B2 | 2/2005 | Lockwood et al. |
| 6,942,633 B2 | 9/2005 | Odland |
| 6,951,553 B2 | 10/2005 | Bubb et al. |
| 6,979,324 B2 | 12/2005 | Bybordi et al. |
| 7,004,915 B2 | 2/2006 | Boynton et al. |
| 7,022,113 B2 | 4/2006 | Lockwood et al. |
| 7,067,709 B2 | 6/2006 | Murata et al. |
| 7,070,584 B2 | 7/2006 | Johnson et al. |
| 7,087,806 B2 | 8/2006 | Scheinberg et al. |
| 7,108,683 B2 | 9/2006 | Zamierowski |
| 7,216,651 B2 | 5/2007 | Argenta et al. |
| 7,338,482 B2 | 3/2008 | Lockwood et al. |
| 7,361,184 B2 | 4/2008 | Joshi |
| 7,524,315 B2 | 4/2009 | Blott et al. |
| 7,553,306 B1 | 6/2009 | Hunt et al. |
| 7,611,500 B1 | 11/2009 | Lina et al. |
| 7,615,036 B2 | 11/2009 | Joshi et al. |
| D605,775 S | 12/2009 | Koch et al. |
| D608,007 S | 1/2010 | Arbesman et al. |
| 7,645,253 B2 | 1/2010 | Gura et al. |
| 7,687,678 B2 | 3/2010 | Jacobs |
| 7,776,028 B2 | 8/2010 | Miller et al. |
| D625,422 S | 10/2010 | Arbesman et al. |
| 7,815,616 B2 | 10/2010 | Boehringer et al. |
| 7,837,673 B2 | 11/2010 | Vogel |
| 7,896,864 B2 | 3/2011 | Lockwood et al. |
| 7,922,676 B2 | 4/2011 | Daskal et al. |
| 7,922,703 B2 | 4/2011 | Riesinger |
| 7,942,866 B2 | 5/2011 | Radl et al. |
| 7,959,624 B2 | 6/2011 | Riesinger |
| 7,976,519 B2 | 7/2011 | Bubb et al. |
| 8,007,257 B2 | 8/2011 | Heaton et al. |
| 8,007,481 B2 | 8/2011 | Schuessler et al. |
| 8,062,272 B2 | 11/2011 | Weston |
| 8,080,702 B2 | 12/2011 | Blott et al. |
| 8,092,441 B2 | 1/2012 | Sugito |
| 8,158,844 B2 | 4/2012 | McNeil |
| 8,167,869 B2 | 5/2012 | Wudyka |
| 8,212,100 B2 | 7/2012 | Moore |
| 8,215,929 B2 | 7/2012 | Shen et al. |
| 8,323,264 B2 | 12/2012 | Weston et al. |
| 8,371,829 B2 | 2/2013 | Jaeb et al. |
| 8,372,049 B2 | 2/2013 | Jaeb et al. |
| 8,404,921 B2 | 3/2013 | Lee et al. |
| 8,409,160 B2 | 4/2013 | Locke et al. |
| 8,414,519 B2 | 4/2013 | Hudspeth et al. |
| 8,419,696 B2 | 4/2013 | Wilkes |
| 8,425,478 B2 | 4/2013 | Olson |
| 8,439,894 B1 | 5/2013 | Miller |
| 8,449,508 B2 | 5/2013 | Coulthard et al. |
| 8,500,776 B2 | 8/2013 | Ebner |
| 8,529,548 B2 | 9/2013 | Blott et al. |
| 8,545,466 B2 | 10/2013 | Andresen et al. |
| 8,603,074 B2 | 12/2013 | Kagan |
| 8,641,691 B2 | 2/2014 | Fink et al. |
| 8,641,693 B2 | 2/2014 | Locke et al. |
| 8,702,665 B2 | 4/2014 | Locke et al. |
| 8,821,458 B2 | 9/2014 | Locke et al. |
| 8,870,837 B2 | 10/2014 | Locke et al. |
| 8,961,496 B2 | 2/2015 | Locke et al. |
| 8,974,429 B2 | 3/2015 | Gordon et al. |
| 9,061,095 B2 | 6/2015 | Adie et al. |
| 9,084,845 B2 | 7/2015 | Adie et al. |
| 9,089,630 B2 | 7/2015 | Perkins et al. |
| 9,198,802 B2 | 12/2015 | Robinson et al. |
| 9,259,558 B2 | 2/2016 | Tsai |
| 9,283,118 B2 | 3/2016 | Locke et al. |
| 9,393,354 B2 | 7/2016 | Freedman et al. |
| 9,414,968 B2 | 8/2016 | Heagle |
| 9,421,133 B2 | 8/2016 | Hu et al. |
| 9,427,505 B2 | 8/2016 | Askem et al. |
| 9,446,176 B2 | 9/2016 | Locke et al. |
| 9,452,088 B2 | 9/2016 | Shulman et al. |
| 9,560,975 B2 | 2/2017 | Mei et al. |
| D787,690 S | 5/2017 | Mackay et al. |
| 9,636,440 B2 | 5/2017 | Weston et al. |
| 9,737,649 B2 | 8/2017 | Begin et al. |
| 9,770,368 B2 | 9/2017 | Robinson et al. |
| 9,814,811 B2 | 11/2017 | Aalders et al. |
| 9,907,703 B2 | 3/2018 | Allen et al. |
| 9,925,092 B2 | 3/2018 | Luckemeyer et al. |
| RE46,778 E | 4/2018 | Peron |
| 9,956,120 B2 | 5/2018 | Locke |
| 10,004,914 B2 | 6/2018 | Nettesheim et al. |
| 10,010,656 B2 | 7/2018 | Jaeb et al. |
| 10,016,544 B2 | 7/2018 | Coulthard et al. |
| 10,046,095 B1 | 8/2018 | Middaugh et al. |
| 10,201,644 B2 | 2/2019 | Haggstrom et al. |
| 10,265,445 B2 | 4/2019 | Weston |
| 10,384,041 B2 | 8/2019 | Patel et al. |
| 10,391,212 B2 | 8/2019 | Joshi et al. |
| 10,463,773 B2 | 11/2019 | Haggstrom et al. |
| 10,660,994 B2 | 5/2020 | Askem et al. |
| 2003/0212357 A1 | 11/2003 | Pace |
| 2004/0076662 A1 | 4/2004 | Riesinger |
| 2004/0087884 A1 | 5/2004 | Haddock et al. |
| 2004/0167482 A1 | 8/2004 | Watson |
| 2005/0012616 A1 | 1/2005 | Forster et al. |
| 2005/0045461 A1 | 3/2005 | Sweetland et al. |
| 2005/0065471 A1 | 3/2005 | Kuntz |
| 2005/0119737 A1 | 6/2005 | Bene et al. |

(56) References Cited

U.S. PATENT DOCUMENTS

| | | |
|---|---|---|
| 2005/0137539 A1 | 6/2005 | Biggie et al. |
| 2006/0029650 A1 | 2/2006 | Coffey |
| 2006/0086598 A1 | 4/2006 | Sneek et al. |
| 2006/0107642 A1 | 5/2006 | Smith et al. |
| 2006/0259102 A1 | 11/2006 | Slatkine |
| 2007/0128055 A1 | 6/2007 | Lee |
| 2007/0179460 A1 | 8/2007 | Adahan |
| 2007/0225663 A1 | 9/2007 | Watt et al. |
| 2007/0255187 A1 | 11/2007 | Branch |
| 2008/0021356 A1 | 1/2008 | Castello Escude |
| 2008/0051716 A1 | 2/2008 | Stutz |
| 2009/0012484 A1 | 1/2009 | Nielsen et al. |
| 2009/0048556 A1 | 2/2009 | Durand |
| 2010/0022990 A1 | 1/2010 | Karpowicz et al. |
| 2010/0100160 A1 | 4/2010 | Edman et al. |
| 2010/0137775 A1 | 6/2010 | Hu et al. |
| 2010/0160881 A1 | 6/2010 | Lin et al. |
| 2010/0280469 A1 | 11/2010 | Hall et al. |
| 2010/0292632 A1 | 11/2010 | Mulvihill et al. |
| 2010/0305490 A1* | 12/2010 | Coulthard ............. A61F 13/022 |
| | | 604/313 |
| 2011/0092927 A1 | 4/2011 | Wilkes et al. |
| 2011/0112492 A1 | 5/2011 | Bharti et al. |
| 2011/0224631 A1 | 9/2011 | Simmons et al. |
| 2011/0292623 A1 | 12/2011 | Stanley |
| 2011/0305736 A1 | 12/2011 | Wieland et al. |
| 2012/0016323 A1* | 1/2012 | Robinson ............. A61M 27/00 |
| | | 604/319 |
| 2012/0035562 A1 | 2/2012 | Locke et al. |
| 2012/0059294 A1 | 3/2012 | Schubert et al. |
| 2012/0109034 A1 | 5/2012 | Locke et al. |
| 2013/0165821 A1* | 6/2013 | Freedman ........... A61M 3/0279 |
| | | 604/20 |
| 2013/0215638 A1 | 8/2013 | Dabov et al. |
| 2014/0005618 A1 | 1/2014 | Locke et al. |
| 2014/0100536 A1 | 4/2014 | Angel |
| 2014/0330227 A1 | 11/2014 | Coulthard et al. |
| 2014/0343518 A1 | 11/2014 | Riesinger |
| 2015/0057625 A1 | 2/2015 | Coulthard |
| 2015/0202354 A1 | 7/2015 | Wall |
| 2016/0015873 A1 | 1/2016 | Robinson et al. |
| 2016/0166438 A1 | 6/2016 | Rovaniemi |
| 2016/0199546 A1 | 7/2016 | Chao |
| 2016/0242964 A1 | 8/2016 | Rapp et al. |
| 2016/0271305 A1 | 9/2016 | Kurihara et al. |
| 2016/0361473 A1 | 12/2016 | Robinson et al. |
| 2017/0112974 A1 | 4/2017 | Fujisaki |
| 2017/0112975 A1 | 4/2017 | Fujisaki |
| 2017/0127525 A1 | 5/2017 | Schonholz |
| 2017/0232189 A1 | 8/2017 | Qin et al. |
| 2017/0296714 A1 | 10/2017 | Locke et al. |
| 2017/0319761 A1 | 11/2017 | Locke et al. |
| 2017/0326277 A1 | 11/2017 | Huang |
| 2017/0368239 A1 | 12/2017 | Askem et al. |
| 2018/0008760 A1 | 1/2018 | Zilbershlag et al. |
| 2018/0021178 A1 | 1/2018 | Locke et al. |
| 2018/0028728 A1 | 2/2018 | Aarestad et al. |
| 2018/0104393 A1 | 4/2018 | Wu et al. |
| 2018/0200414 A1 | 7/2018 | Askem et al. |
| 2018/0272052 A1 | 9/2018 | Locke et al. |
| 2018/0296397 A1 | 10/2018 | Askem et al. |
| 2018/0311078 A1 | 11/2018 | Hartwell |
| 2018/0318137 A1 | 11/2018 | Donda et al. |
| 2018/0318165 A1 | 11/2018 | Donda et al. |
| 2018/0353771 A1 | 12/2018 | Kim et al. |
| 2019/0021911 A1 | 1/2019 | Askem et al. |
| 2019/0125943 A1 | 5/2019 | Askem et al. |
| 2019/0142644 A1 | 5/2019 | Askem et al. |
| 2019/0142647 A1 | 5/2019 | Hartwell |
| 2019/0143007 A1 | 5/2019 | Askem et al. |
| 2019/0159938 A1 | 5/2019 | Askem et al. |
| 2019/0192350 A1 | 6/2019 | Gowans et al. |
| 2019/0201594 A1* | 7/2019 | Shelton, IV ........ H04L 63/1416 |
| 2019/0247236 A1* | 8/2019 | Sides ..................... A61M 1/98 |
| 2019/0282737 A1* | 9/2019 | Beadle ................... A61F 13/05 |
| 2020/0022846 A1 | 1/2020 | Beadle et al. |
| 2020/0061379 A1* | 2/2020 | Bogie ................. A61F 13/0253 |
| 2020/0338243 A1* | 10/2020 | Harrison ............... A61M 1/962 |
| 2021/0001019 A1* | 1/2021 | Elder ................... A61M 1/918 |
| 2021/0001022 A1 | 1/2021 | Lin |
| 2021/0060216 A1* | 3/2021 | Long ....................... A61M 1/91 |
| 2021/0077670 A1* | 3/2021 | Long ....................... A61M 1/73 |
| 2021/0260258 A1* | 8/2021 | Kodavanti .............. A61F 13/05 |
| 2022/0168152 A1* | 6/2022 | Locke ................... A61M 1/985 |
| 2024/0024565 A1 | 1/2024 | Laitenberger et al. |

FOREIGN PATENT DOCUMENTS

| | | |
|---|---|---|
| DE | 19844355 A1 | 4/2000 |
| EP | 0512543 A2 | 11/1992 |
| EP | 1411874 A1 | 4/2004 |
| EP | 1455701 B1 | 3/2006 |
| EP | 1448261 B1 | 2/2007 |
| EP | 1807032 A1 | 7/2007 |
| EP | 1476217 B1 | 3/2008 |
| EP | 1931413 A2 | 6/2008 |
| EP | 1507498 B1 | 7/2009 |
| EP | 1791579 B1 | 7/2009 |
| EP | 2109427 A1 | 10/2009 |
| EP | 1947987 B1 | 5/2010 |
| EP | 1358456 B1 | 7/2010 |
| EP | 1807031 B1 | 7/2010 |
| EP | 2214728 A2 | 8/2010 |
| EP | 2254537 A2 | 12/2010 |
| EP | 2255839 A1 | 12/2010 |
| EP | 2279016 A1 | 2/2011 |
| EP | 2326295 A1 | 6/2011 |
| EP | 2335749 A1 | 6/2011 |
| EP | 2340064 A1 | 7/2011 |
| EP | 2344217 A1 | 7/2011 |
| EP | 2346468 A2 | 7/2011 |
| EP | 2349155 A2 | 8/2011 |
| EP | 1814609 B2 | 9/2011 |
| EP | 2205190 B1 | 9/2011 |
| EP | 2370116 A2 | 10/2011 |
| EP | 2345438 B1 | 9/2012 |
| EP | 2531761 A1 | 12/2012 |
| EP | 2231088 B1 | 1/2013 |
| EP | 2015655 B1 | 3/2013 |
| EP | 2285323 B1 | 3/2013 |
| EP | 2545946 A3 | 3/2013 |
| EP | 2563421 A1 | 3/2013 |
| EP | 2049055 B1 | 4/2013 |
| EP | 2340066 B1 | 4/2013 |
| EP | 2440260 B1 | 5/2013 |
| EP | 2340062 B1 | 6/2013 |
| EP | 2603699 A1 | 6/2013 |
| EP | 1893145 B1 | 7/2013 |
| EP | 2370142 B1 | 7/2013 |
| EP | 2279017 B1 | 8/2013 |
| EP | 2370117 B1 | 8/2013 |
| EP | 2258443 B1 | 9/2013 |
| EP | 2263742 B1 | 9/2013 |
| EP | 2558139 B1 | 10/2013 |
| EP | 1848390 B1 | 12/2013 |
| EP | 1875081 B1 | 12/2013 |
| EP | 2271381 B1 | 12/2013 |
| EP | 2345436 B1 | 12/2013 |
| EP | 2361641 B1 | 12/2013 |
| EP | 2160166 B1 | 1/2014 |
| EP | 1565219 B1 | 2/2014 |
| EP | 2305325 B1 | 4/2014 |
| EP | 2323712 B1 | 4/2014 |
| EP | 2345437 B1 | 4/2014 |
| EP | 2451498 B1 | 4/2014 |
| EP | 2051675 B1 | 6/2014 |
| EP | 1485613 B1 | 7/2014 |
| EP | 1545644 B1 | 8/2014 |
| EP | 2349154 B1 | 8/2014 |
| EP | 2146759 B1 | 9/2014 |
| EP | 2416816 B1 | 10/2014 |
| EP | 2468323 B1 | 10/2014 |
| EP | 2658493 B1 | 10/2014 |
| EP | 1850818 B1 | 12/2014 |

(56)            References Cited

FOREIGN PATENT DOCUMENTS

| | | | |
|---|---|---|---|
| EP | 2268348 | B1 | 12/2014 |
| EP | 2561128 | B1 | 1/2015 |
| EP | 2829287 | A1 | 1/2015 |
| EP | 2683285 | B1 | 2/2015 |
| EP | 2470136 | B1 | 3/2015 |
| EP | 2503974 | B1 | 5/2015 |
| EP | 2249894 | B1 | 8/2015 |
| EP | 2802366 | B1 | 8/2015 |
| EP | 2438302 | B1 | 9/2015 |
| EP | 2346545 | B1 | 10/2015 |
| EP | 2438301 | B1 | 10/2015 |
| EP | 2802304 | B1 | 12/2015 |
| EP | 2852421 | B1 | 1/2016 |
| EP | 2410962 | B1 | 3/2016 |
| EP | 2640436 | B1 | 3/2016 |
| EP | 2855937 | B1 | 5/2016 |
| EP | 2433594 | B1 | 6/2016 |
| EP | 2919730 | B1 | 6/2016 |
| EP | 2861869 | B1 | 7/2016 |
| EP | 2945584 | B1 | 7/2016 |
| EP | 2293749 | B1 | 8/2016 |
| EP | 3072542 | A2 | 9/2016 |
| EP | 2305327 | B1 | 10/2016 |
| EP | 2467086 | B1 | 10/2016 |
| EP | 2470135 | B1 | 10/2016 |
| EP | 2767305 | B1 | 10/2016 |
| EP | 2282788 | B1 | 12/2016 |
| EP | 2462956 | B2 | 3/2017 |
| EP | 3139878 | A1 | 3/2017 |
| EP | 2249761 | B1 | 4/2017 |
| EP | 2731563 | B1 | 5/2017 |
| EP | 2905037 | B1 | 5/2017 |
| EP | 2968871 | B1 | 7/2017 |
| EP | 2632613 | B1 | 8/2017 |
| EP | 2781208 | B1 | 8/2017 |
| EP | 2888478 | B1 | 8/2017 |
| EP | 2937107 | B1 | 8/2017 |
| EP | 2967627 | B1 | 8/2017 |
| EP | 3062751 | B1 | 8/2017 |
| EP | 3139879 | B1 | 8/2017 |
| EP | 2359784 | B1 | 9/2017 |
| EP | 3151795 | B1 | 9/2017 |
| EP | 2367518 | B1 | 10/2017 |
| EP | 2675493 | B1 | 10/2017 |
| EP | 3068455 | B1 | 10/2017 |
| EP | 2558046 | B2 | 11/2017 |
| EP | 2666489 | B1 | 11/2017 |
| EP | 2736548 | B1 | 11/2017 |
| EP | 3052158 | B1 | 11/2017 |
| EP | 2558045 | B1 | 12/2017 |
| EP | 2593058 | B1 | 3/2018 |
| EP | 3127577 | B1 | 3/2018 |
| EP | 3139880 | B1 | 3/2018 |
| EP | 2868300 | B1 | 6/2018 |
| EP | 1496822 | B1 | 8/2018 |
| EP | 2879633 | B1 | 8/2018 |
| EP | 2227203 | B1 | 9/2018 |
| EP | 2696826 | B1 | 9/2018 |
| EP | 3106186 | B1 | 9/2018 |
| EP | 3162330 | B1 | 9/2018 |
| EP | 3169382 | B1 | 9/2018 |
| EP | 3203953 | B1 | 9/2018 |
| EP | 2941280 | B1 | 10/2018 |
| EP | 3244852 | B1 | 10/2018 |
| EP | 2974754 | B1 | 11/2018 |
| EP | 3062753 | B1 | 11/2018 |
| EP | 3235525 | B1 | 11/2018 |
| EP | 3120879 | B1 | 12/2018 |
| EP | 3191149 | B1 | 1/2019 |
| EP | 2370130 | B1 | 3/2019 |
| EP | 3053609 | B1 | 3/2019 |
| EP | 3180048 | B1 | 3/2019 |
| EP | 3143974 | B1 | 4/2019 |
| EP | 2558140 | B2 | 5/2019 |
| EP | 2285432 | B2 | 6/2019 |
| EP | 3187209 | B1 | 6/2019 |
| EP | 3050545 | B1 | 7/2019 |
| EP | 3311856 | B1 | 7/2019 |
| EP | 3319656 | B1 | 8/2019 |
| EP | 2355762 | B1 | 9/2019 |
| EP | 2822613 | B1 | 9/2019 |
| EP | 2863855 | B1 | 9/2019 |
| EP | 2482912 | B1 | 10/2019 |
| EP | 3038667 | B1 | 10/2019 |
| EP | 3129095 | B1 | 10/2019 |
| EP | 3191150 | B1 | 10/2019 |
| EP | 3280466 | B1 | 10/2019 |
| EP | 3287113 | B1 | 10/2019 |
| EP | 3281650 | B1 | 11/2019 |
| EP | 2244756 | B1 | 12/2019 |
| EP | 2968702 | B1 | 12/2019 |
| EP | 3053554 | B1 | 12/2019 |
| EP | 2785390 | B1 | 10/2020 |
| FR | 2939320 | A1 | 6/2010 |
| GB | 2511523 | A | 9/2014 |
| JP | H04354722 | A | 12/1992 |
| RU | 131622 | U1 | 8/2013 |
| WO | WO-2008039223 | A1 | 4/2008 |
| WO | WO-2009098696 | A2 | 8/2009 |
| WO | WO-2009120951 | A2 | 10/2009 |
| WO | WO-2011130570 | A1 | 10/2011 |
| WO | WO-2011135285 | A1 | 11/2011 |
| WO | WO-2011144888 | A1 | 11/2011 |
| WO | WO-2012078781 | A1 | 6/2012 |
| WO | WO-2012171318 | A1 | 12/2012 |
| WO | WO-2014099709 | A1 | 6/2014 |
| WO | WO-2015135040 | A1 | 9/2015 |
| WO | WO-2016126560 | A1 | 8/2016 |
| WO | WO-2017079174 | A1 | 5/2017 |
| WO | WO-2017196888 | A1 | 11/2017 |
| WO | WO-2018056060 | A1 | 3/2018 |
| WO | WO-2018115461 | A1 | 6/2018 |
| WO | WO-2018156730 | A1 | 8/2018 |
| WO | WO-2018158250 | A1 | 9/2018 |
| WO | WO-2018162613 | A1 | 9/2018 |
| WO | WO-2018164803 | A1 | 9/2018 |
| WO | WO-2018185138 | A1 | 10/2018 |
| WO | WO-2018192978 | A1 | 10/2018 |
| WO | WO-2018206420 | A1 | 11/2018 |
| WO | WO-2019053101 | A1 | 3/2019 |
| WO | WO-2019053106 | A1 | 3/2019 |
| WO | WO-2019086332 | A1 | 5/2019 |
| WO | WO-2019086341 | A1 | 5/2019 |
| WO | WO-2019086475 | A1 | 5/2019 |
| WO | WO-2019193141 | A1 | 10/2019 |
| WO | WO-2019211730 | A1 | 11/2019 |
| WO | WO-2020110626 | A1 | 6/2020 |
| WO | WO-2021239656 | A1 | 12/2021 |
| WO | WO-2022238919 | A1 | 11/2022 |

OTHER PUBLICATIONS

International Preliminary Report on Patentability for Application No. PCT/EP2021/076022, mailed on Apr. 20, 2023, 8 pages.

* cited by examiner

100

160

161

1500

1081

1710

1068

1072

1068

1074

2200

LAT_OUT

LAT_OUT

2202

Q1

Q6B

R14

2250

TP21

4    3

2240

C16

R19

2210

R53

TP23

2238

2232

1    2234

5

U2

+    2222

4    −    3    C29    C30

2226    2224

R13    R16

2

2220

2204

TEMPERATURE MONITORING AND CONTROL FOR NEGATIVE PRESSURE WOUND THERAPY SYSTEMS

CROSS-REFERENCE TO RELATED APPLICATIONS

This application is a U.S. national stage application of International Patent Application No. PCT/EP2021/076022, filed Sep. 22, 2021, which claims priority to U.K. Patent Application No. 2015747.5, filed on Oct. 5, 2020 and U.K. Patent Application No. 2104922.6, filed Apr. 7, 2021, the disclosure of each of which is hereby incorporated by reference in its entirety.

TECHNICAL FIELD

Embodiments described herein relate to apparatuses, systems, and methods the treatment of wounds, for example using dressings in combination with negative pressure wound therapy.

DESCRIPTION OF THE RELATED ART

The treatment of open or chronic wounds that are too large to spontaneously close or otherwise fail to heal by means of applying negative pressure to the site of the wound is well known in the art. Negative pressure wound therapy ("NPWT") systems currently known in the art commonly involve placing a cover that is impermeable or semi-permeable to fluids over the wound, using various means to seal the cover to the tissue of the patient surrounding the wound, and connecting a source of negative pressure (such as a vacuum pump) to the cover in a manner so that negative pressure is created and maintained under the cover. It is believed that such negative pressures promote wound healing by facilitating the formation of granulation tissue at the wound site and assisting the body's normal inflammatory process while simultaneously removing excess fluid, which may contain adverse cytokines and/or bacteria. However, further improvements in NPWT are needed to fully realize the benefits of treatment.

SUMMARY

A negative pressure wound therapy system can include a negative pressure source that can be configured to provide negative pressure to a wound of a patient covered by a wound dressing. The negative pressure system can include a first sensor that can be configured to measure a temperature of at least a first portion of the negative pressure system. The negative pressure system can include a second sensor that can be configured to measure a temperature of at least one of the patient or at least a second portion of the negative pressure system. The negative pressure system can include electronic control circuitry that can be configured to control operation of the negative pressure source responsive to the temperature measured by the first sensor. The negative pressure system can include a controller that can be configured to control operation of the negative pressure source responsive to temperature measured by the second sensor. The controller can be programmable. The controller can be configured to control operation of the negative pressure source independently of the electronic control circuitry.

The negative pressure wound therapy system of the preceding paragraph and/or any of the negative pressure wound therapy systems, apparatuses, or devices disclosed herein can include one or more of the following features. The controller can be configured to reduce activity of the negative pressure source responsive to temperature measured by the second sensor satisfying a second temperature threshold that is lower than the first temperature threshold and not satisfying the first temperature threshold. Reducing activity of the negative pressure source can include lowering a duty cycle of the negative pressure source. The negative pressure wound therapy system can include the wound dressing. At least one of the negative pressure source, the first sensor, the second sensor, the electronic control circuitry, or the controller can be at least partially supported by the wound dressing. The temperature measured by the first sensor can be indicative of a temperature of the negative pressure source. The electronic control circuitry can be configured to deactivate the negative pressure source responsive to a determination that the temperature measured by the first sensor satisfies a temperature threshold indicative of unsafe operation. The electronic control circuitry can include a comparator configured to output the determination that the temperature measured by the first sensor satisfies the temperature threshold indicative of unsafe operation. The comparator can accept as a first input the temperature measured by the first sensor. The comparator can accept as a second input the temperature threshold. The comparator can be configured to operate in a presence of noise as a result of at least one of: one or more the inputs of the comparator being filtered or a feedback being provided between the first or second input of the comparator and an output of the comparator. The first and second inputs of the comparator can be low-pass filtered. The feedback can include a resistor positioned between a non-inverting input of the comparator and the output of the comparator. The negative pressure wound therapy system can include a power source that can be configured to provide power at least to the negative pressure source. The negative pressure wound therapy system can include a boost converter that can be configured to increase power provided by the power source and provide the increased power to the negative pressure source. The first sensor can be configured to measure temperature of the boost converter. The first sensor can be positioned proximal to the boost converter.

The negative pressure wound therapy system of any of the preceding paragraphs and/or any of the negative pressure wound therapy systems, apparatuses, or devices disclosed herein can include one or more of the following features. The second sensor can include a pair of sensors. The controller can be configured to determine a temperature of at least one of the negative pressure source or another component of the negative pressure system based on a difference between measurements of first and second sensors of the pair of sensors. The first and second sensors of the pair of sensors can be configured to measure pressure and temperature. The first sensor of the pair of sensors can be positioned at an inlet of the negative pressure source and second sensor of the pair of sensors can be positioned at an exhaust of the negative pressure source. The controller can be configured to control operation of the negative pressure source responsive to temperature measured by the second sensor by at least one of: deactivating the negative pressure source in response to temperature measured by the second sensor satisfying a first temperature threshold indicative of unsafe operation, reducing activity of the negative pressure source responsive to temperature measured by the second sensor satisfying a second temperature threshold smaller than the first temperature threshold and not satisfying the first temperature threshold, or taking no action responsive to temperature measured by the second sensor not satisfying the second temperature threshold. Reducing activity of the negative pressure source can include reducing a duty cycle of the negative pressure source. The controller can be configured to store in a memory a first indication that at least one of the first or second temperature thresholds has been satisfied and a second indication that the temperature measured by the first sensor satisfies a temperature threshold indicative of unsafe operation.

The negative pressure wound therapy system of any of the preceding paragraphs and/or any of the negative pressure wound therapy systems, apparatuses, or devices disclosed herein can include one or more of the following features. The controller can be configured to disable activation of the negative pressure source responsive to a determination that the temperature measured by at least one of the first sensor or the second sensor satisfies a temperature threshold indicative of unsafe operation. The first and second portions of the negative pressure system can be the same. The negative pressure wound therapy system can include a switch that can be configured to permit activation of the negative pressure source. The switch can be configured to be deactivated responsive to a determination that the temperature measured by at least one of the first sensor or the second sensor satisfies a temperature threshold indicative of unsafe operation. The second sensor can be configured to measure temperature of the patient. The controller can be configured to deactivate the negative pressure source responsive to a determination that the temperature measured by the second sensor satisfies a temperature threshold indicative of high patient temperature. The controller can be configured to execute instructions to control operation of the negative pressure source responsive to temperature measured by the second sensor.

Disclosed are methods of operating the negative pressure wound therapy system of any of the preceding paragraphs and/or any of the negative pressure wound therapy systems, apparatuses, or devices disclosed herein.

DETAILED DESCRIPTION

Figure 1A:
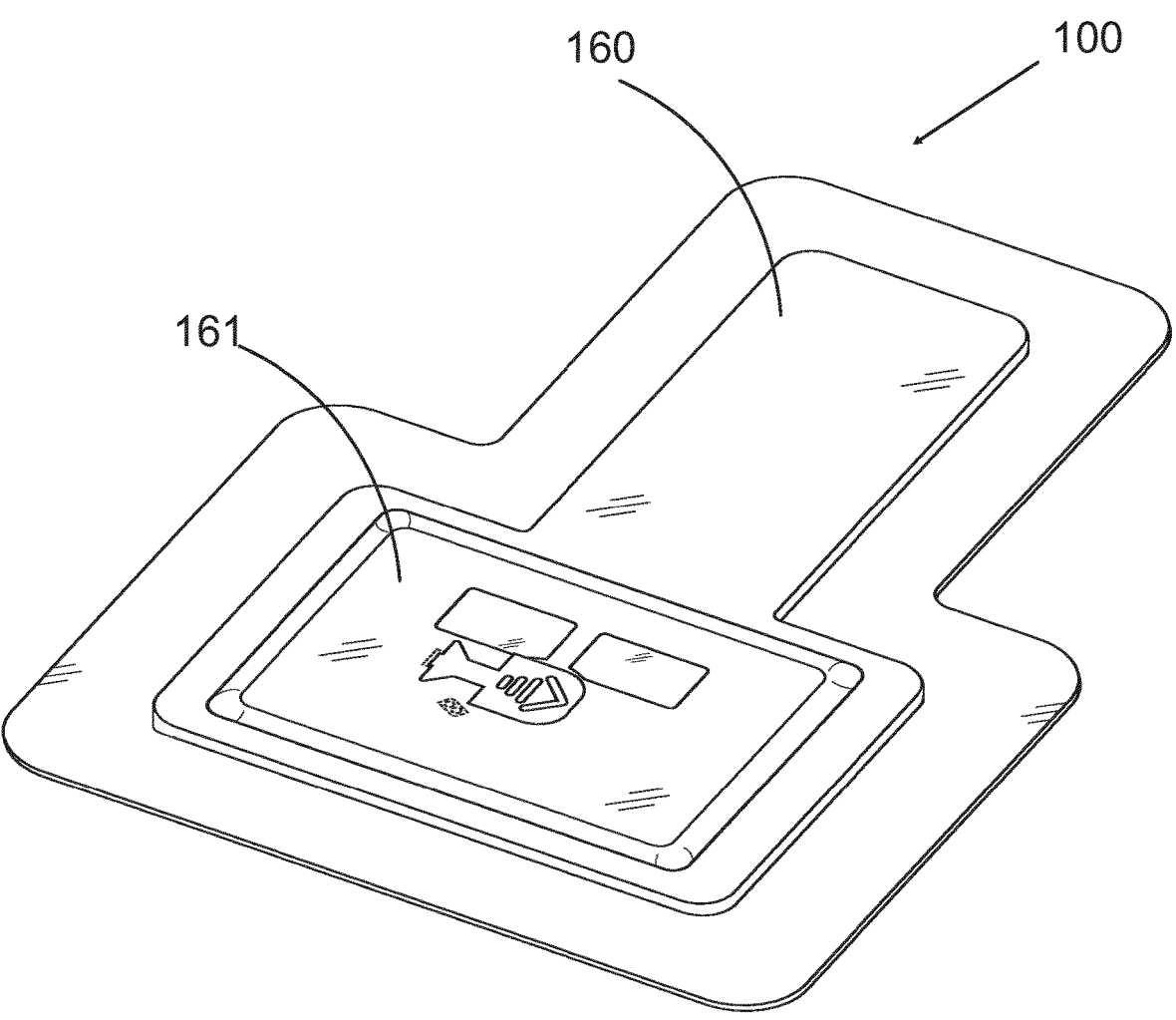
FIGS. 1A-1C illustrate a wound dressing incorporating a source of negative pressure and/or other electronic components within the wound dressing.

Embodiments disclosed herein relate to apparatuses and methods of treating a wound with reduced pressure, including a source of negative pressure and wound dressing components and apparatuses. These apparatuses and components, including but not limited to wound overlays, backing layers, cover layers, drapes, sealing layers, spacer layers, absorbent layers, transmission layers, wound contact layers, packing materials, fillers and/or fluidic connectors are sometimes collectively referred to herein as dressings.

It will be appreciated that throughout this specification reference is made to a wound. It is to be understood that the term wound is to be broadly construed and encompasses open and closed wounds in which skin may be torn, cut or punctured or where trauma causes a contusion, or any other superficial or other conditions or imperfections on the skin of a patient or otherwise that benefit from reduced pressure treatment. A wound is thus broadly defined as any damaged region of tissue where fluid may or may not be produced. Examples of such wounds include, but are not limited to, abdominal wounds or other large or incisional wounds, either as a result of surgery, trauma, sterniotomies, fasciotomies, or other conditions, dehisced wounds, acute wounds, chronic wounds, subacute and dehisced wounds, traumatic wounds, flaps and skin grafts, lacerations, abrasions, contusions, burns, diabetic ulcers, pressure ulcers, stoma, surgical wounds, trauma and venous ulcers or the like.

It will be understood that embodiments of the present disclosure are generally applicable to use in NPWT or topical negative pressure ("TNP") therapy systems. Briefly, negative pressure wound therapy assists in the closure and healing of many forms of "hard to heal" wounds by reducing tissue oedema; encouraging blood flow and granular tissue formation; removing excess exudate and may reduce bacterial load (and thus infection risk). In addition, the therapy allows for less disturbance of a wound leading to more rapid healing. TNP therapy systems may also assist on the healing of surgically closed wounds by removing fluid and by helping to stabilize the tissue in the apposed position of closure. A further beneficial use of TNP therapy can be found in grafts and flaps where removal of excess fluid is important and close proximity of the graft to tissue is required in order to ensure tissue viability.

As is used herein, reduced or negative pressure levels, such as $-X$ mmHg, represent pressure levels relative to normal ambient atmospheric pressure, which can correspond to 760 mmHg (or 1 atm, 29.93 inHg, 101.325 kPa, 14.696 psi, 1013.25 mbar, etc.). Accordingly, a negative pressure value of $-X$ mmHg reflects absolute pressure that is X mmHg below 760 mmHg or, in other words, an absolute pressure of (760-X) mmHg. In addition, negative pressure that is "less" or "smaller" than X mmHg corresponds to pressure that is closer to atmospheric pressure (such as, $-40$ mmHg is less than $-60$ mmHg). Negative pressure that is "more" or "greater" than $-X$ mmHg corresponds to pressure that is further from atmospheric pressure (such as, $-80$ mmHg is more than $-60$ mmHg). In some cases, local ambient atmospheric pressure is used as a reference point, and such local atmospheric pressure may not necessarily be, for example, 760 mmHg.

The negative pressure range can be approximately −80 mmHg, or between about −20 mmHg and −200 mmHg. Note that these pressures are relative to normal ambient atmospheric pressure, which can be 760 mmHg. Thus, −200 mmHg would be about 560 mmHg in practical terms. In some cases, the pressure range can be between about −40 mmHg and −50 mmHg. Alternatively, a pressure range of up to −75 mmHg, up to −80 mmHg or over −80 mmHg can be used. Also in some cases a pressure range of below −75 mmHg can be used. Alternatively, a pressure range of over approximately −100 mmHg, or even −150 mmHg, can be supplied by the negative pressure apparatus.

Wound Dressing

Figure 1B:
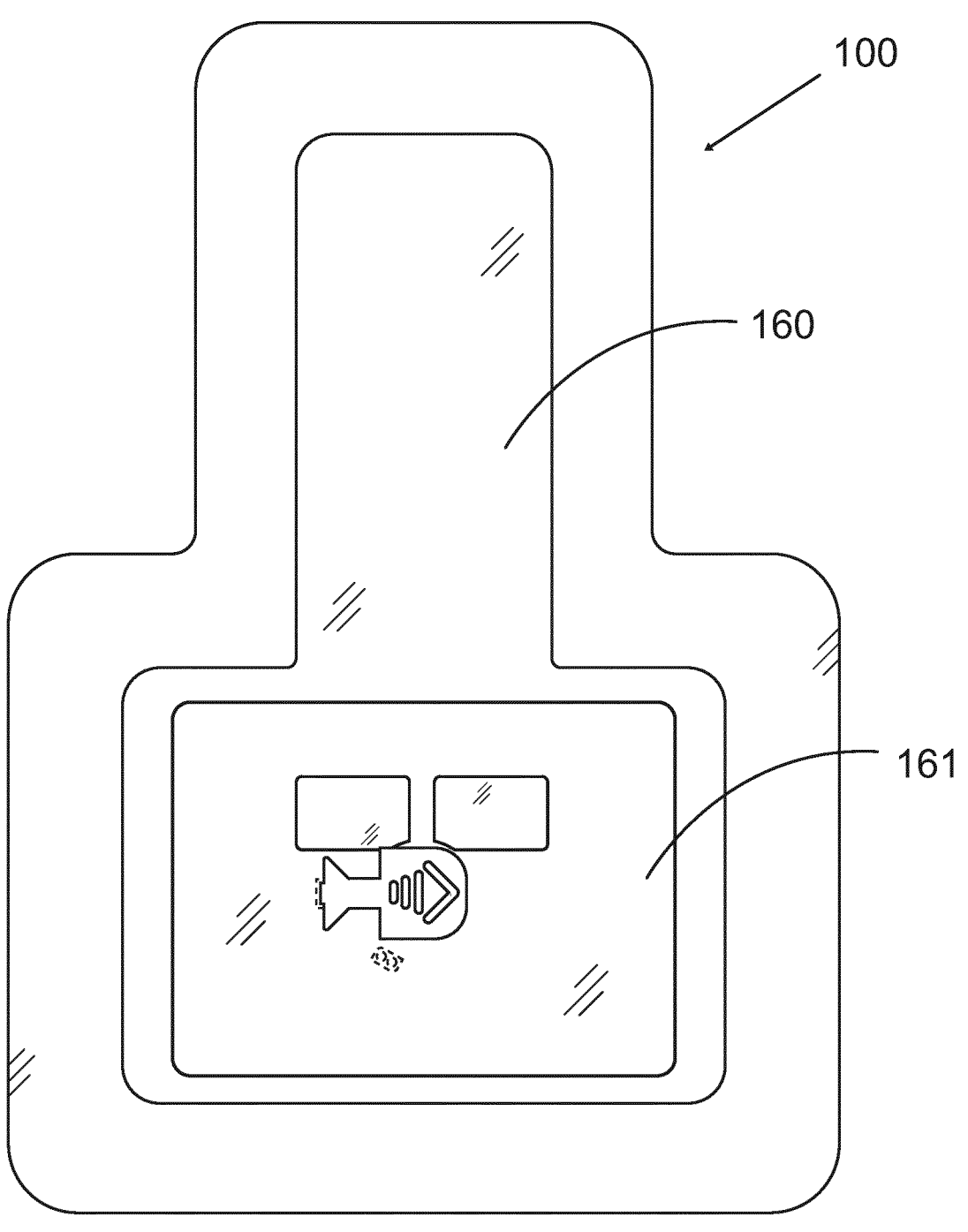
Figure 1C:
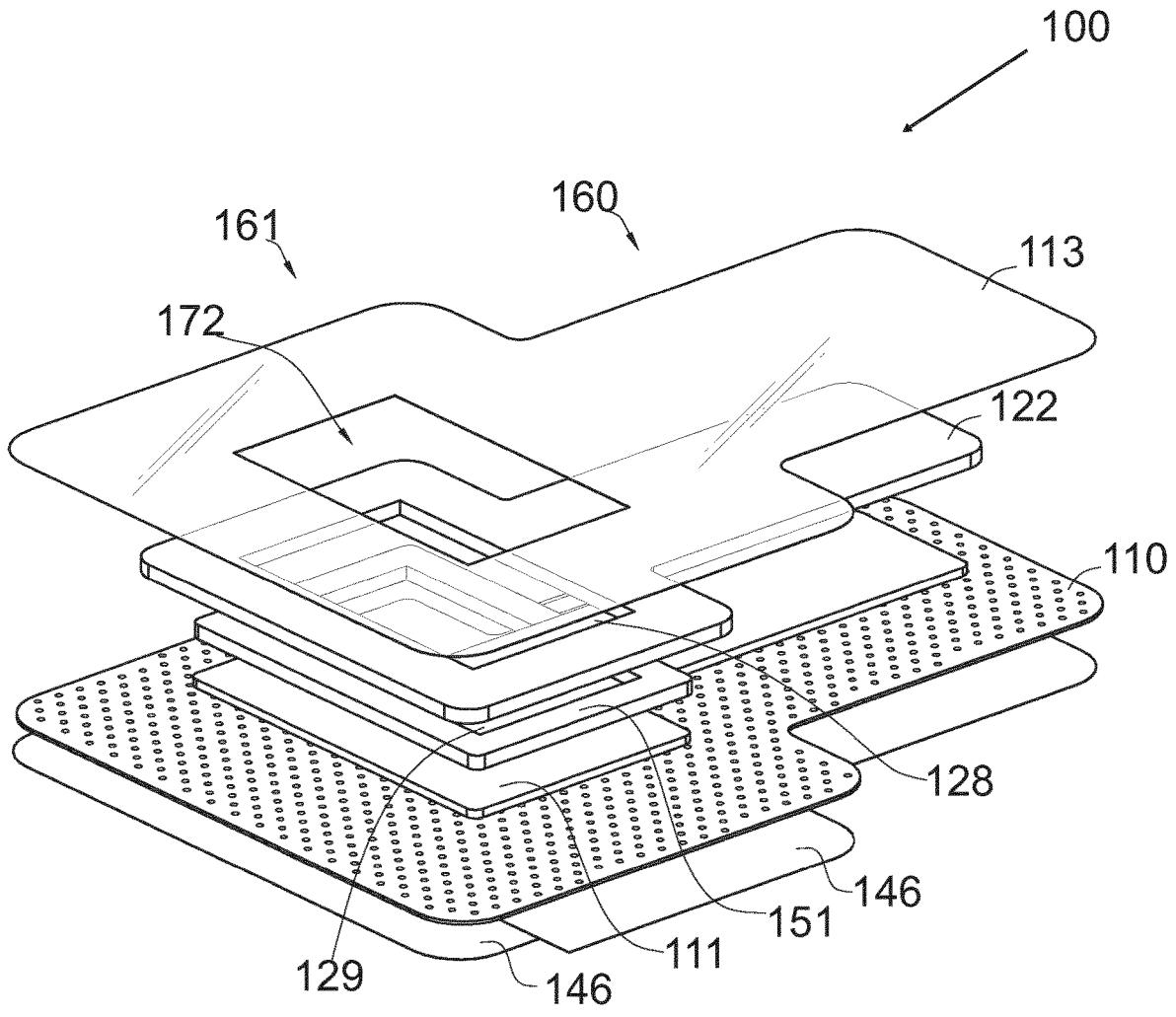

A source of negative pressure (such as a pump) and some or all other components of the TNP system, such as power source(s), sensor(s), connector(s), user interface component(s) (such as button(s), switch(es), speaker(s), screen(s), etc.) and the like, can be integral with the wound dressing. The material layers can include a wound contact layer, one or more absorbent layers, one or more transmission or spacer layers, and a backing layer or cover layer covering the one or more absorbent and transmission or spacer layers. The wound dressing can be placed over a wound and sealed to the wound with the pump and/or other electronic components contained under the cover layer within the wound dressing. The dressing can be provided as a single article with all wound dressing elements (including the pump) pre-attached and integrated into a single unit. A periphery of the wound contact layer can be attached to the periphery of the cover layer enclosing all wound dressing elements as illustrated in FIG. 1A-1C.

The pump and/or other electronic components can be configured to be positioned adjacent to or next to the absorbent and/or transmission layers so that the pump and/or other electronic components are still part of a single article to be applied to a patient. The pump and/or other electronics can be positioned away from the wound site. Although certain features disclosed herein may be described as relating to systems and method for controlling operation of a negative pressure wound therapy system in which the pump and/or other electronic components are positioned in or on the wound dressing, the systems and methods disclosed herein are applicable to any negative pressure wound therapy system or any medical device. FIGS. 1A-1C illustrate a wound dressing incorporating the source of negative pressure and/or other electronic components within the wound dressing. FIGS. 1A-1C illustrate a wound dressing 100 with the pump and/or other electronics positioned away from the wound site. The wound dressing can include an electronics area 161 and an absorbent area 160. The dressing can comprise a wound contact layer 110 (not shown in FIGS. 1A-1B) and a moisture vapor permeable film, cover layer or backing layer 113 positioned above the contact layer and other layers of the dressing. The wound dressing layers and components of the electronics area as well as the absorbent area can be covered by one continuous cover layer 113 as shown in FIGS. 1A-1C.

A layer 111 of porous material can be located above the wound contact layer 110. As used herein, the terms porous material, spacer, and/or transmission layer can be used interchangeably to refer to the layer of material in the dressing configured to distribute negative pressure throughout the wound area. This porous layer, or transmission layer, 111 allows transmission of fluid including liquid and gas away from a wound site into upper layers of the wound dressing. In particular, the transmission layer 111 preferably ensures that an open air channel can be maintained to communicate negative pressure over the wound area even when the absorbent layer has absorbed substantial amounts of exudates. The layer 111 should preferably remain open under the typical pressures that will be applied during negative pressure wound therapy as described above, so that the whole wound site sees an equalized negative pressure. The layer 111 may be formed of a material having a three dimensional structure. For example, a knitted or woven spacer fabric (for example Baltex 7970 weft knitted polyester) or a non-woven fabric could be used.

Further, one or more absorbent layers (such as layers 122, 151) for absorbing and retaining exudate aspirated from the wound can be utilized. A superabsorbent material can be used in the absorbent layers 122, 151. The one or more layers 122, 151 of absorbent material may be provided above the transmission layer 111. Since in use each of the absorbent layers experiences negative pressures, the material of the absorbent layer can be chosen to absorb liquid under such circumstances. The absorbent layers 122. 151 may comprise a composite comprising superabsorbent powder, fibrous material such as cellulose, and bonding fibers. The composite can be an airlaid, thermally-bonded composite.

The electronics area 161 can include a source of negative pressure (such as a pump) and some or all other components of the TNP system, such as power source(s), sensor(s), connector(s), user interface component(s) (such as button(s), switch(es), speaker(s), screen(s), etc.) and the like, that can be integral with the wound dressing. For example, the electronics area 161 can include a button or switch (shown in FIGS. 1A-1B as being covered by a pull tab). The button or switch can be used for operating the pump (such as, turning the pump on/off).

The electronics area 161 of the dressing can comprise one or more layers of transmission or spacer material and/or absorbent material and electronic components can be embedded within the one or more layers of transmission or spacer material and/or absorbent material. The layers of transmission or absorbent material can have recesses or cut outs to embed the electronic components within whilst providing structure to prevent collapse. As shown in FIG. 1C, recesses 128 and 129 can be provided in absorbent layers 151 and 122, respectively.

As used herein the upper layer, top layer, or layer above refers to a layer furthest from the surface of the skin or wound while the dressing is in use and positioned over the wound. Accordingly, the lower surface, lower layer, bottom layer, or layer below refers to the layer that is closest to the surface of the skin or wound while the dressing is in use and positioned over the wound. Additionally, the layers can have a proximal wound-facing face referring to a side or face of the layer closest to the skin or wound and a distal face referring to a side or face of the layer furthest from the skin or wound.

The cover layer may include a cutout 172 positioned over at least a portion of the aperture 128 in the absorbent layer 122 to allow access and fluid communication to at least a portion of the absorbent layers 122 and 151, transmission layer 111, and would contact layer 110 positioned below. An electronics assembly such as described below can be positioned in the apertures 128, 129, and 172 of the first and second absorbent material 151 and 122 and the cover layer 113. The electronics assembly can include a pump, power source, and a printed circuit board as described with reference to FIGS. 3 and 4A-4B.

Before use, the dressing can include one or more delivery layers 146 adhered to the bottom surface of the wound contact layer. The delivery layer 146 can cover adhesive or apertures on the bottom surface of the wound contact layer 110. The delivery layer 146 can provided support for the dressing and can assist in sterile and appropriate placement of the dressing over the wound and skin of the patient. The delivery layer 146 can include handles that can be used by the user to separate the delivery layer 146 from the wound contact layer 110 before applying the dressing to a wound and skin of a patient.

Electronics Assembly Incorporated Within the Wound Dressing

Figures 2A, 2B:
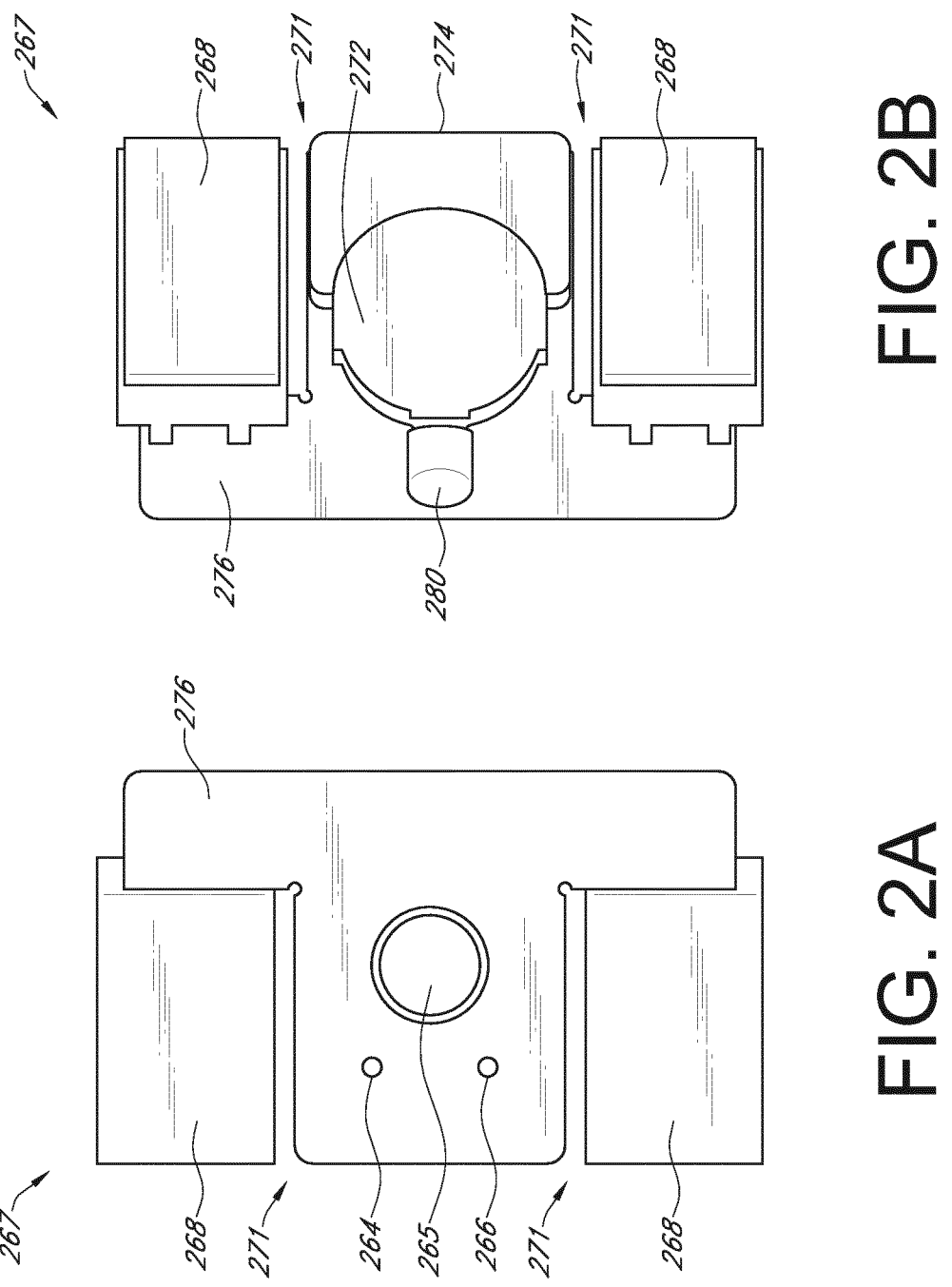
FIGS. 2A-2B illustrate an electronics unit that may be incorporated into a wound dressing.

FIGS. 2A-2B illustrate an electronics unit 267 that can be incorporated into a wound dressing. FIG. 2A illustrates the top view of the electronics unit. FIG. 2B illustrates a bottom or wound facing surface of the electronics unit. The electronics unit 267 can include a pump 272 and one or more power sources 268, such as batteries. The electronics unit 267 can include a circuit board 276 configured to be in electrical communication with the pump 272 and/or power source 268. The circuit board 276 can be flexible or substantially flexible.

As illustrated in FIG. 2A, the electronics unit 267 can include single button or switch 265 on the upper surface of the unit. The single button or switch 265 can be used as an on/off button or switch to stop and start operation of the pump and/or electronic components. The electronics unit 267 can also include one or more vents or exhaust apertures 264 on the circuit board 276 for expelling the air exhausted from the pump. As shown in FIG. 2B, a pump outlet exhaust mechanism 274 (sometimes referred to as pump exhaust mechanism or pump outlet mechanism) can be attached to the outlet of the pump 272.

The electronics unit 267 can include a pump inlet protection mechanism 280 as shown in FIG. 2B positioned on the portion of the electronics unit closest to the absorbent area and aligned with the inlet of the pump 272. The pump inlet protection mechanism 280 is positioned between the pump inlet and the absorbent area or absorbent layer of the dressing. The pump inlet protection mechanism 280 can include hydrophobic material to prevent fluid from entering the pump 272. The pump inlet protection mechanism 280 (or any of the inlet protection mechanisms disclosed herein) can include a filter.

The upper surface of the electronics unit 267 can include one or more indicators 266 for indicating a condition of the pump and/or level of pressure within the dressing. The indicators can be small LED lights or other light source that are visible through the dressing components or through holes in the dressing components above the indicators. The indicators can be green, yellow, red, orange, or any other color. For example, there can be two lights, one green light and one orange light. The green light can indicate the device is working properly and the orange light can indicate that there is some issue with the pump (such as, leak, saturation level of the dressing, blockage downstream of the pump, exhaust blockage, low battery, or the like).

The power source 268 can be in electrical communication with the circuit board 276. One or more power source connections are connected to a surface of the circuit board 276. The circuit board 276 can have other electronics incorporated within. For example, the circuit board 276 may support various sensors including, but not limited to, one or more pressure sensors, temperature sensors, optic sensors and/or cameras, and/or saturation indicators.

Figure 3:
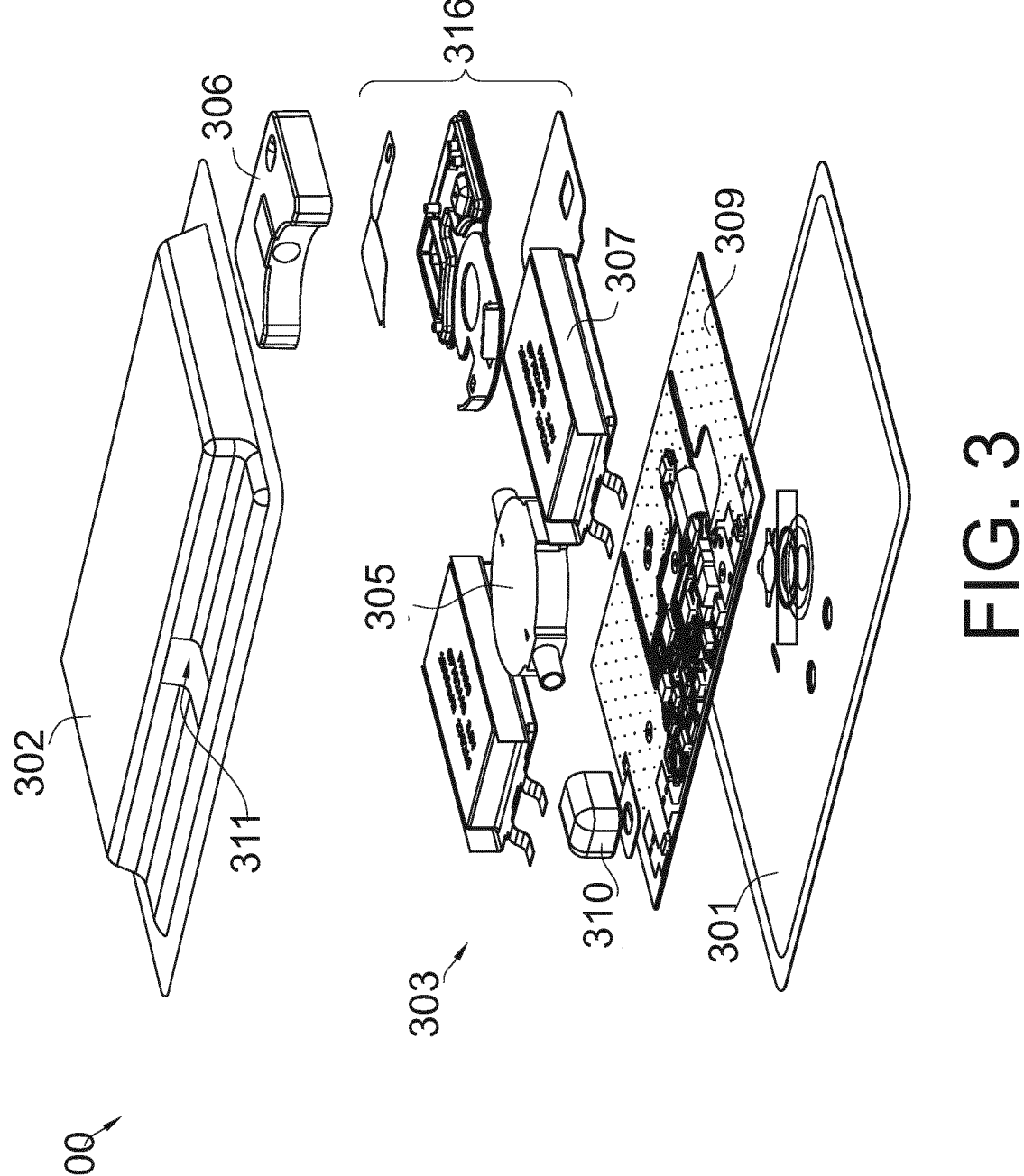
FIG. 3 is an exploded perspective view of an electronics assembly enclosing an electronics unit within a housing.

FIG. 3 illustrates an electronics assembly 300 enclosing an electronics unit within a housing. As illustrated in FIG. 3, the housing of the electronics assembly 300 can include a plate 301 and flexible film 302 enclosing the electronics unit 303 within. The electronics unit 303 can include a pump 305, inlet protection mechanism 310, pump exhaust mechanism 306, power source 307, and circuit board 309. The circuit board 309 can be flexible or substantially flexible.

As is illustrated, the pump exhaust mechanism 306 can be an enclosure, such as a chamber. The electronics unit 303 and pump 305 can be used without the inlet protection mechanism 310. However, the pump exhaust mechanism 306 and the pump 305 can sit within an extended casing 316.

The flexible film 302 can be attached to the plate 301 to form a fluid tight seal and enclosure around the electronic components. The flexible film 302 can be attached to the plate at a perimeter of the plate by heat welding, adhesive bonding, ultrasonic welding, RF welding, or any other attachment or bonding technique.

The flexible film 302 can include an aperture 311. The aperture 311 can allow the inlet protection mechanism 310 to be in fluid communication with the absorbent and/or transmission layers of the wound dressing. The perimeter of the aperture 311 of the flexible film 303 can be sealed or attached to the inlet protection mechanism 310 to form a fluid tight seal and enclosure around the inlet protection mechanism 310 allowing the electronic components 303 to remain protected from fluid within the dressing. The flexible film 302 can be attached to the inlet protection mechanism 310 at a perimeter of the inlet protection mechanism 310 by heat welding, adhesive bonding, ultrasonic welding, RF welding, or any other attachment or bonding technique. The inlet protection mechanism 310 can prevent wound exudate or liquids from the wound and collected in the absorbent area 160 of the wound dressing from entering the pump and/or electronic components of the electronics assembly 300.

The electronics assembly 300 illustrated in FIG. 3 can be incorporated within the wound dressing such that, once the dressing is applied to the body of the patient, air from within the dressing can pass through the inlet protection mechanism 310 to be pumped out toward the pump exhaust mechanism 306 in communication with an aperture in the casing 316 and the circuit board 309 as described herein.

Figure 4A:
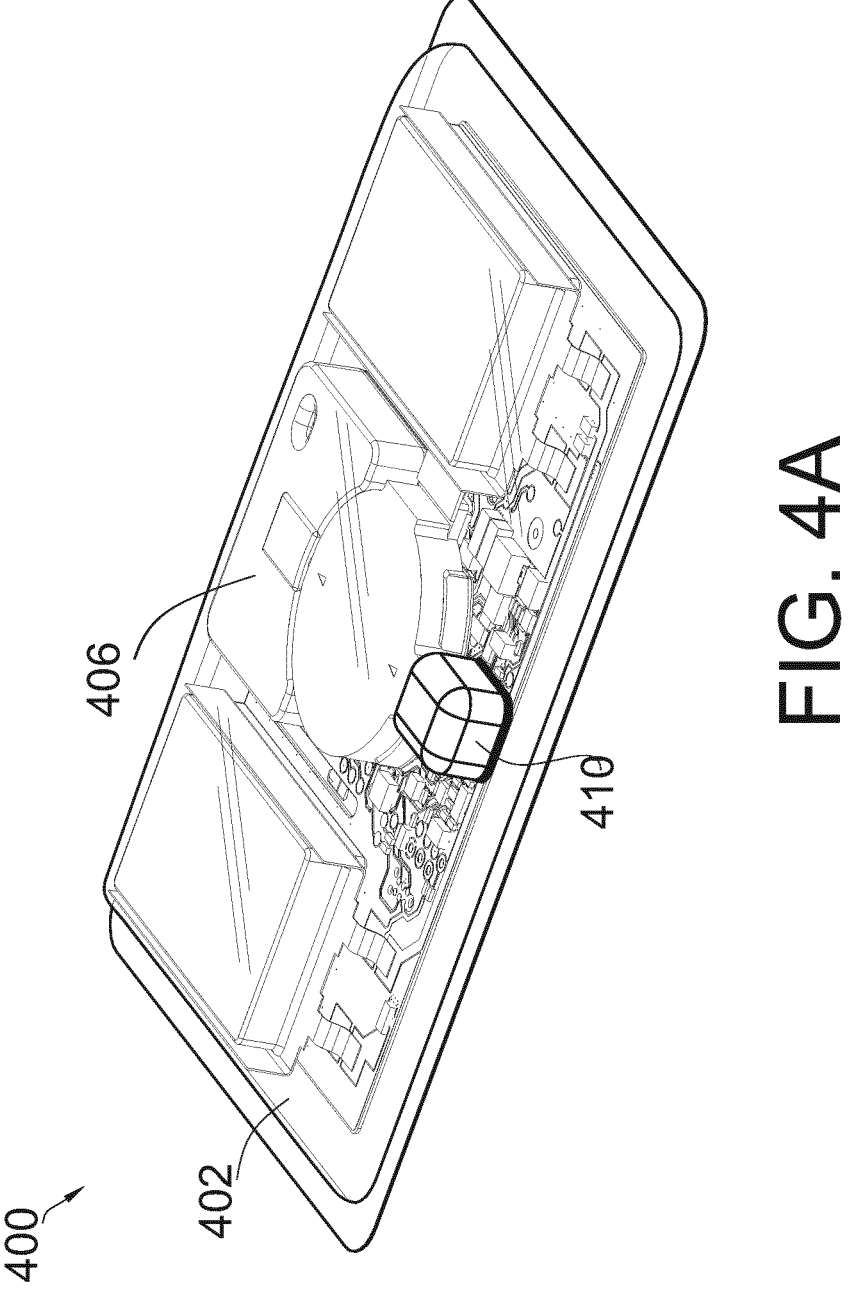
FIG. 4A illustrates a bottom perspective view of the electronics assembly of FIG. 3.
Figure 4B:
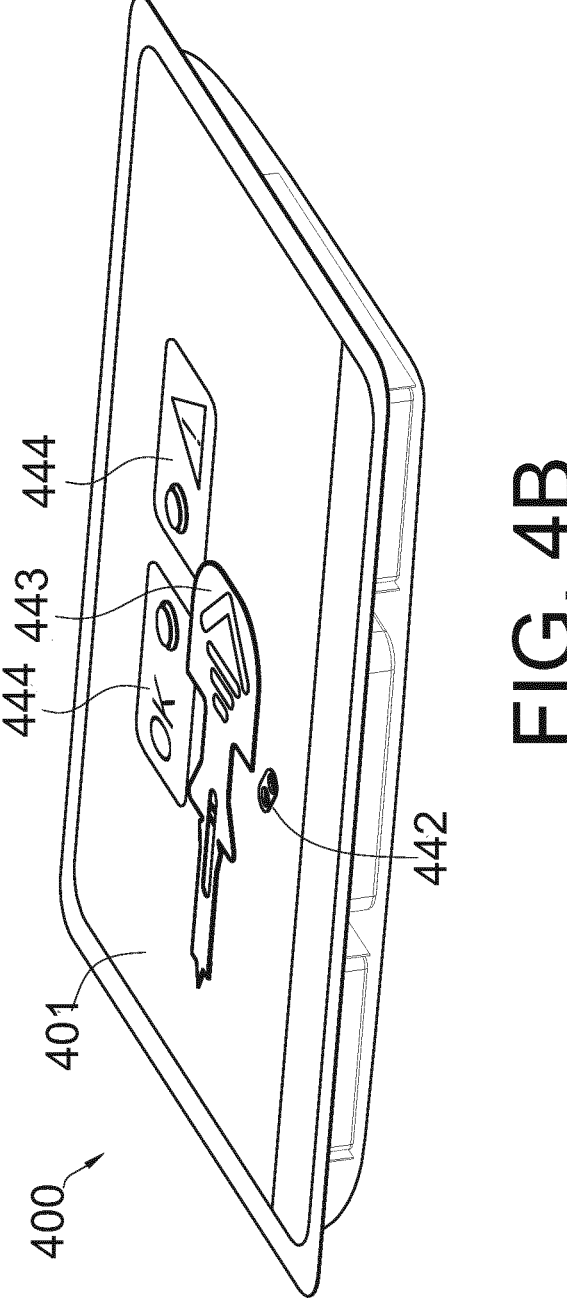
FIG. 4B illustrates a top perspective view of the electronics assembly of FIG. 3.

FIGS. 4A-B illustrate an electronics assembly 400 including a pump inlet protection mechanism 410 sealed to the exterior of the flexible film 402, similar to the description with reference to FIG. 3. Also shown is an exhaust mechanism 406, which can be similar to the exhaust mechanism 306.

FIG. 4A illustrates lower, wound facing surface of the electronics assembly 400. FIG. 4B shows an upper surface of the plate 401 (which can face the patient or user) of the electronics assembly 400. The upper surface of the plate 401 can include an on/off switch or button cover 443 (illustrated as a pull tab), indicators 444, and/or one or more vent holes 442. Removal of the pull tab 443 can cause activation of the electronics assembly 400, such as provision of power from the power source to the electronics assembly. Further details of operation of the pull tab 443 are described in PCT International Application No. PCT/EP2018/079745, filed Oct. 30, 2018, titled "SAFE OPERATION OF INTEGRATED NEGATIVE PRESSURE WOUND TREATMENT APPARATUSES," which is incorporated by reference in its entirety herein.

The electronics assembly 400 with the pump inlet protection mechanism 410 extending from and sealed to the film 402 can be positioned within the aperture 172 in the cover layer 113 and absorbent layer(s) (122, 151) as shown in FIG. 1C. The perimeter of the electronics assembly 400 can be sealed to a top surface of the outer perimeter of the aperture 172 in the cover layer 113 as shown in FIG. 1C and described in more detail with reference to FIG. 5A-5B herein. The electronics assembly 400 can be sealed to the cover layer 113 with a sealant gasket, adhesive, heat welding, adhesive bonding, ultrasonic welding, RF welding, or any other attachment or bonding technique. The electronics assembly 400 can be permanently sealed to the cover layer 113 and could not be removed from the cover layer without destroying the dressing.

The electronics assembly 400 can be utilized in a single dressing and disposed of with the dressing. In some cases, the electronics assembly 400 can be utilized in a series of dressings.

Figure 5A:
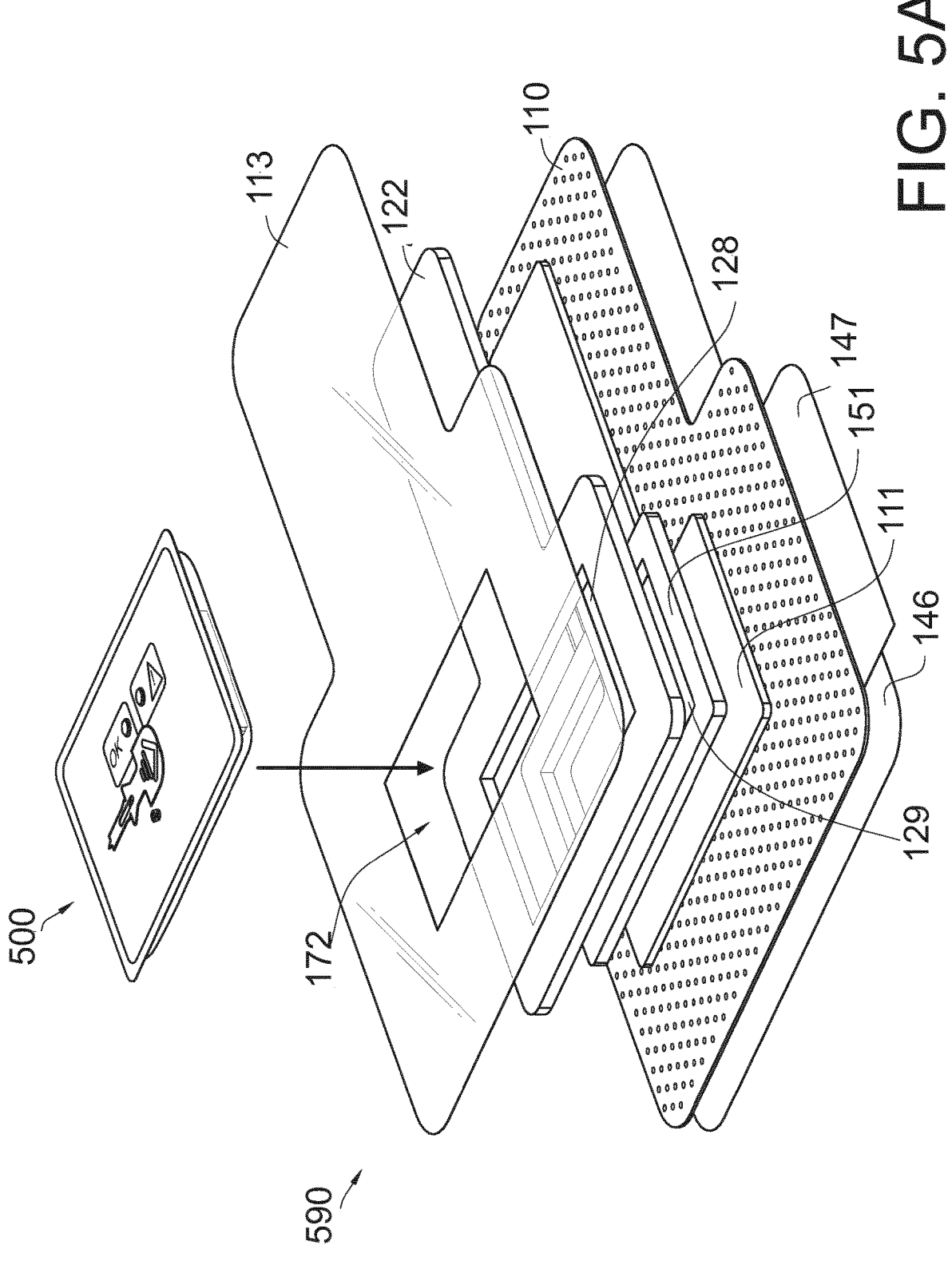
FIG. 5A is an exploded view of a wound dressing incorporating an electronics assembly within the wound dressing layers.
Figure 5B:
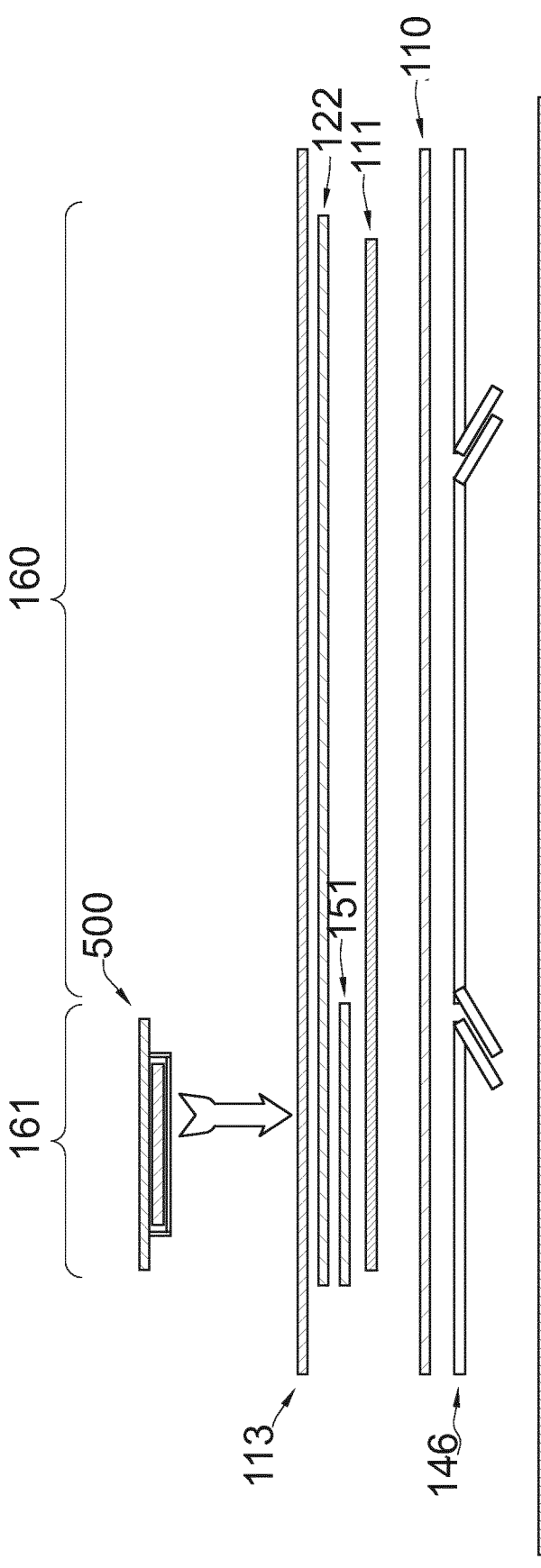
FIG. 5B illustrates a cross sectional layout of the material layers of a wound dressing incorporating an electronics assembly within the dressing.

FIG. 5A illustrates a wound dressing, such as the one in FIG. 1C, incorporating an electronics assembly 500 within the wound dressing layers 590. FIG. 5B illustrates a cross-sectional view of the wound dressing incorporating the electronics assembly of FIG. 5A. The electronics assembly 500 can be provided within the aperture 172 in the cover layer and apertures 129 and 128 in the first and second absorbent layers 122, 151. The electronics assembly 500 can seal to the outer perimeter of the aperture 172 of the cover layer. The dressing can comprise a wound contact layer 110 and a moisture vapor permeable film, cover layer or backing layer 113 positioned above the contact layer 110 and other layers of the dressing. A layer 111 of porous material can be located above the wound contact layer 110. As used herein, the terms porous material, spacer, and/or transmission layer can be used interchangeably to refer to the layer of material in the dressing configured to distribute negative pressure throughout the wound area. This porous layer, or transmission layer, 111 allows transmission of fluid including liquid and gas away from a wound site into upper layers of the wound dressing. Further, one or more absorbent layers (such as layers 122, 151) for absorbing and retaining exudate aspirated from the wound can be utilized. The one or more layers 122, 151 of absorbent material may be provided above the transmission layer 111. There may be a small apertured absorbent layer 151 and a large aperture absorbent layer 122. The small apertured absorbent layer 151 can be positioned on top of the large apertured absorbent layer 122. In some cases, the small apertured absorbent layer 151 can be positioned below of the large apertured absorbent layer 122. Before use, the dressing can include one or more delivery layers 146 adhered to the bottom surface of the wound contact layer. The delivery layer 146 can cover adhesive or apertures on the bottom surface of the wound contact layer 110.

FIGS. 6A-6B and 7A-7B illustrate an electronics assembly 1500 with a pump inlet protection mechanism 1710 and pump exhaust mechanism 1074 on a pump 1072. The assembly 1500 can include cavities 1082 and 1083 (shown in FIGS. 7A-7B) on the pump inlet protection mechanism 1710 and pump exhaust mechanism 1074, respectively. The inlet protection and pump exhaust mechanisms can be adhered to the inlet and the outlet of the pump as described herein. The assembly 1500 can be assembled using an adhesive and allowed to cure prior to incorporating into the electronics assembly.

The pump inlet can be covered or fitted with a pump inlet protection mechanism 1710. The pump inlet protection 1710 can be pushed onto the pump inlet as illustrated by the arrows in FIG. 7A. This can be a friction fit. The port of the pump inlet protection 1710 that receives a portion of the pump inlet can be sized and shaped to be a complementary fit around the pump inlet. The pump inlet protection 1710 can be bonded onto the pump inlet using a silicone sealant or any other sealant or sealing technique. FIG. 7B illustrates the pump inlet protection mechanism 1710 covering the pump inlet and the pump exhaust mechanism 1074 covering the pump outlet. The pump exhaust mechanism 1074 can include one or more apertures or vents 1084 to allow gas aspirated by the pump to be exhausted from the pump exhaust mechanism 1074. In some cases, a non-return valve and/or filter membrane of the pump exhaust mechanism is included in the pump exhaust mechanism 1074.

Figure 6A:
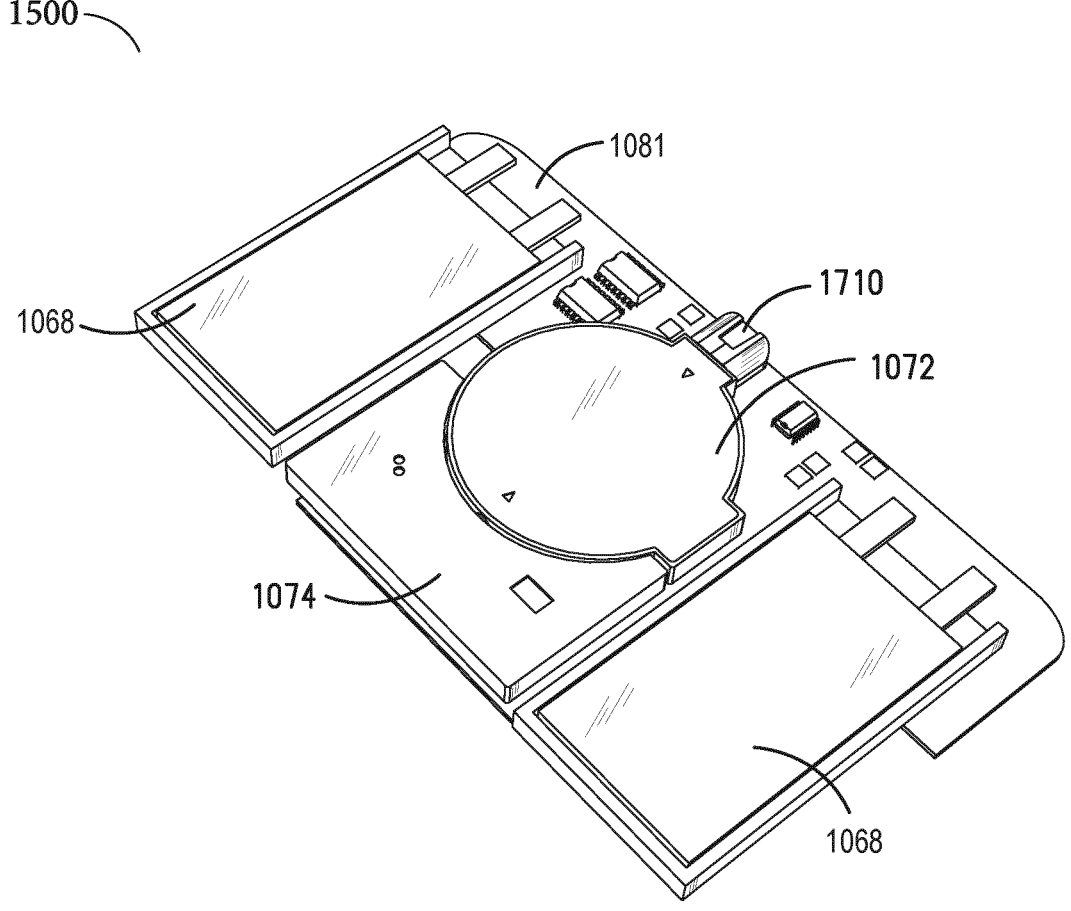
FIGS. 6A-6B and 7A-7B illustrate components of an electronics assembly.
Figure 6B:
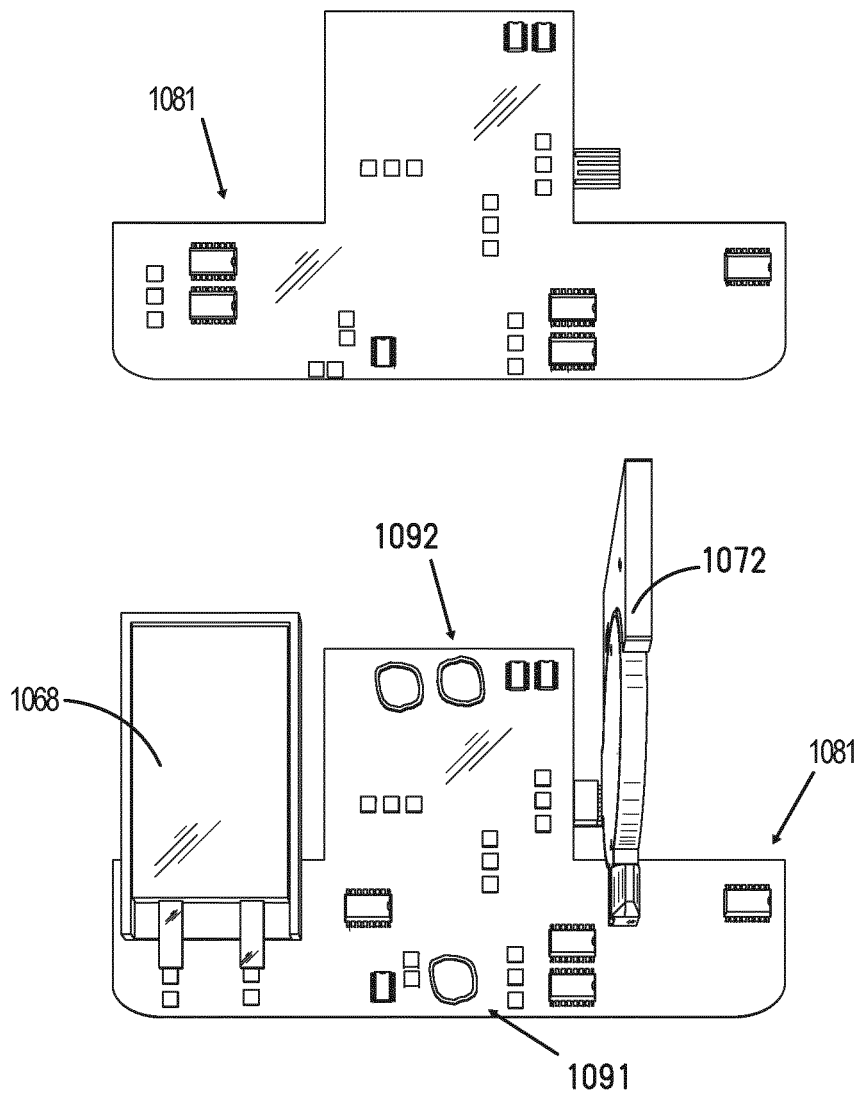
Figure 7A:
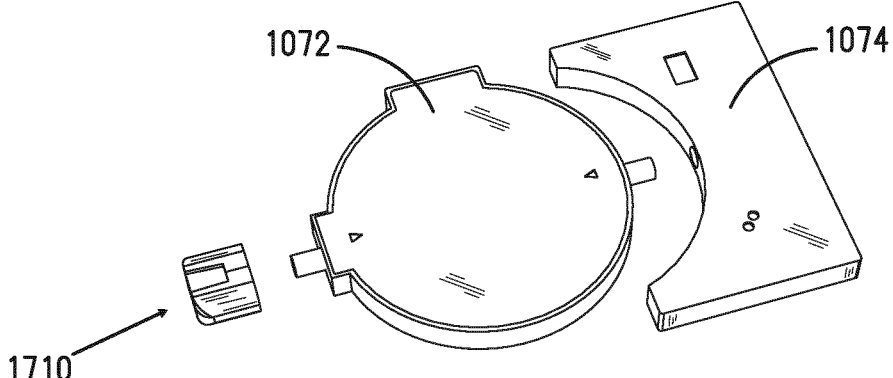
Figure 7B:
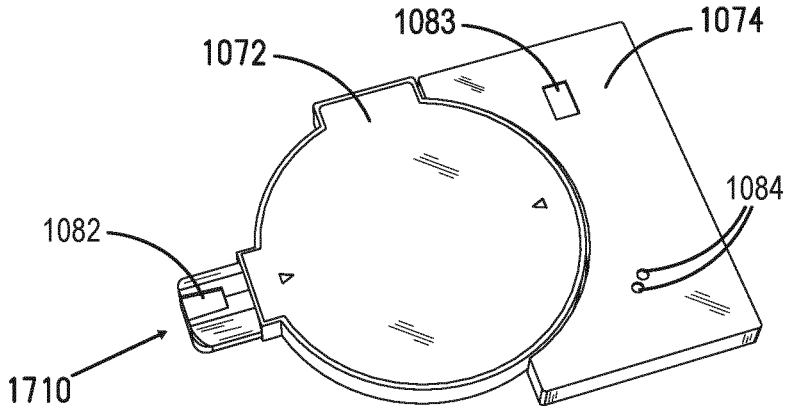

FIGS. 7A-7B illustrate the pump inlet protection mechanism 1710 and pump exhaust mechanism 1074 with cavities 1082 and 1083. A pump assembly including the pump inlet protection mechanism 1710 and pump exhaust mechanism 1074 can be placed over the surface of a circuit board 1081. When the pump assembly is in contact with the surface of the circuit board 1081, the cavities 1082 and 1083 can at least partially enclose sensors on the circuit board 1081, for example, pressure sensors 1091 and 1092 on the circuit board 1081, as illustrated in FIG. 6B.

The pressure sensors 1091 and 1902 illustrated in FIG. 6B can be used to measure and/or monitor the pressure level at the wound and atmospheric pressure. The pressure sensor 1091 can be used to measure and/or monitor pressure at the wound (such as, underneath the wound dressing), which can be accomplished by measuring and/or monitoring pressure in a fluid flow path connecting the negative pressure source or pump 1072 and the wound. The pressure sensor 1091 can measure and/or monitor pressure in the cavity 1082 of the pump inlet protection mechanism 1710 shown in FIGS. 7A-7B. A power source 1068 (illustrated as two batteries in FIG. 6A) can provide power to the negative pressure source 1072 and the electronics.

The pressure sensor 1092 can be used to measure and/or monitor pressure external to the wound dressing. The pressure sensor 1092 can measure and/or monitor pressure in the cavity 1083 of the pump exhaust mechanism 1074 shown in FIGS. 7A-7B. The pressure sensor 1092 can measure pressure external to the wound dressing, which can be relative atmospheric pressure since the atmospheric pressure varies depending on, for instance, an altitude of use or pressurized environment in which the TNP apparatus may be used. These measurements can be used to establish a desired negative pressure differential (or set point) at the wound relative to the external pressure.

The circuit board 1081 (including any of the circuit boards described herein) can include control circuitry, such as one or more processors or controllers, that can control the supply of negative pressure by the negative pressure source 1072 according at least to a comparison between the pressure monitored by the pressure sensor 1091 and the pressure monitored by the pressure sensor 1092. Control circuity can operate the negative pressure source 1072 in a first mode (that can be referred to as an initial pump down mode) in which the negative pressure source 1072 is activated to establish the negative pressure set point at the wound. The set point can be set to, for example, a value in the range between about −70 mmHg to about −90 mmHg, among others. Once the set point has been established, which can be verified based on a difference between pressure measured by the pressure sensor 1091 (or wound pressure) and pressure measured by the pressure sensor 1092 (or external pressure), control circuitry can deactivate (or pause) operation of the negative pressure source 1072. Control circuitry can operate the negative pressure source 1072 is a second mode (that can be referred to as maintenance pump down mode) in which the negative pressure source 1072 is periodically activated to re-establish the negative pressure set point when the wound is depressurized as a result of one or more leaks. Control circuitry can activate the negative pressure source 1072 in response to the pressure at the wound (as monitored by the pressure sensor 1091) becomes more positive than a nega- tive pressure threshold, which can be set to the same negative pressure as the set point or lower negative pressure.

Embodiments of the wound dressings, wound treatment apparatuses and methods described herein may also be used in combination or in addition to one or more features described in PCT International Application No. PCT/EP2017/060464, filed May 3, 2017, titled NEGATIVE PRESSURE WOUND THERAPY DEVICE ACTIVATION AND CONTROL, U.S. Pat. Nos. 8,734,425, and 8,905,985, each of which is hereby incorporated by reference in its entirety herein.

One or more self-adhesive gaskets can be applied to the pump inlet protection mechanism 1710 and pump exhaust mechanism 1074 to seal the cavities 1082 and 1083 of the pump inlet and pump exhaust around sensors on the circuit board 1081 and to seal around the exhaust mechanism vent(s) and corresponding vent(s) in the circuit board 1081 (as described herein). A pre-formed adhesive sheet can be used to form the sealing gaskets between the cavities 1082 and 1083 of the pump inlet and pump exhaust mechanisms and sensors on the circuit board 1081 and between the exhaust mechanism vent(s) and vent(s) in the circuit board 1081. In some cases, an adhesive can be used to seal the cavities 1082 and 1083 of the pump inlet protection 1710 and pump exhaust mechanism 1074 around sensors on the circuit board 1081 and to seal around the exhaust mecha- nism vent(s) 1084 and corresponding vent(s) in the circuit board (see 1094 in FIG. 10B). As described herein, the electronics assembly 1500 can be embedded within layers of the dressing, such as in cutouts or recesses into which the electronics assembly can be placed.

The pump inlet protection mechanism 1710 can provide a large surface area available for vacuum to be drawn by the inlet of the pump. A pump inlet (shown as rounded protru- sion in FIG. 7A) can fit within a recess in the pump inlet protection mechanism 1710. The pump inlet can be attached by friction fit and/or form a complementary fit to the recess of the pump inlet protection mechanism.

The pump inlet protection mechanism 1710 can allow air or gas to pass through, but can block liquid from reaching the negative pressure source. The pump inlet protection mechanism 1710 can include a porous material. The pump inlet protection mechanism 1710 can comprise one or more porous polymer molded components. The pump inlet pro- tection mechanism 1710 can include hydrophobic or sub- stantially hydrophobic material. Material included in the pump inlet protection mechanism 1710 can have a pore size in the range of approximately 5 microns to approximately 40 microns. In some cases, the pore size can be approximately 10 microns. The pump inlet protection mechanism 1710 can include a polymer that can be one of hydrophobic polyeth- ylene or hydrophobic polypropylene. In some cases, the pump inlet protection mechanism can include a Porvair Vyon material with a pore size of 10 microns. Any of the pump inlet protection mechanism described herein can include one or more features of the pump inlet protection mechanism 1710.

Figure 8:
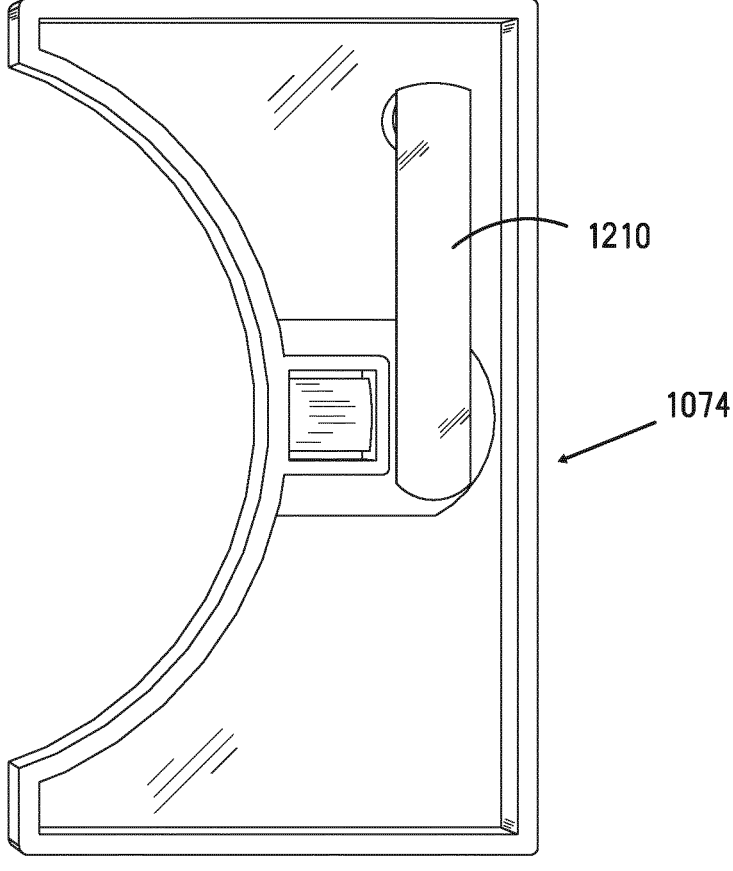
FIG. 8 illustrates a pump outlet mechanism.

The pump exhaust mechanism 1074 (or any of the pump exhaust or outlet mechanisms described herein) can include a check valve or a non-return valve 1210 as shown in FIG. 8. The non-return valve 1210 can be any suitable mechanical one-way valve, such as, for example, a reed valve, a duckbill valve, a ball valve, a loose leaf valve or an umbrella valve, among others. The non-return valve can be similar to any of the non-return valves described in PCT International Appli- cation No. PCT/EP2017/055225, filed Mar. 6, 2017, titled WOUND TREATMENT APPARATUSES AND METH- ODS WITH NEGATIVE PRESSURE SOURCE INTE- GRATED INTO WOUND DRESSING, which is incorpo- rated by reference herein in its entirety. The pump exhaust mechanism 1074 can be bonded to the outlet of the pump using a sealant, for example a silicone sealant. The outlet or exhaust of the pump exhaust mechanism 1074 can include an antimicrobial film and/or other filter membrane that filters gas exhausted outside the NPWT system, such as to the atmosphere. As illustrated, pump exhaust mechanism 1074 can be an enclosure or chamber that is substantially sealed to prevent ingress of gas or fluid other than through the vent(s) 1084.

Any of the embodiments described herein can addition- ally or alternatively include one or more features described in International Application No. PCT/EP2018/074694, filed Sep. 13, 2018, titled NEGATIVE PRESSURE WOUND TREATMENT APPARATUSES AND METHODS WITH INTEGRATED ELECTRONICS, International Application No. PCT/EP2018/074701, filed Sep. 13, 2018, titled NEGA- TIVE PRESSURE WOUND TREATMENT APPARA- TUSES AND METHODS WITH INTEGRATED ELEC- TRONICS, International Application No. PCT/EP2018/079345, filed Oct. 25, 2018, titled NEGATIVE PRESSURE WOUND TREATMENT APPARATUSES AND METH- ODS WITH INTEGRATED ELECTRONICS, International Application No. PCT/EP2020/056317, filed Mar. 10, 2020, titled EXHAUST BLOCKAGE DETECTION FOR NEGA- TIVE PRESSURE WOUND TREATMENT APPARA- TUSES, each of which is incorporated by reference herein in its entirety.

Temperature Monitoring and Control

Figure 9:
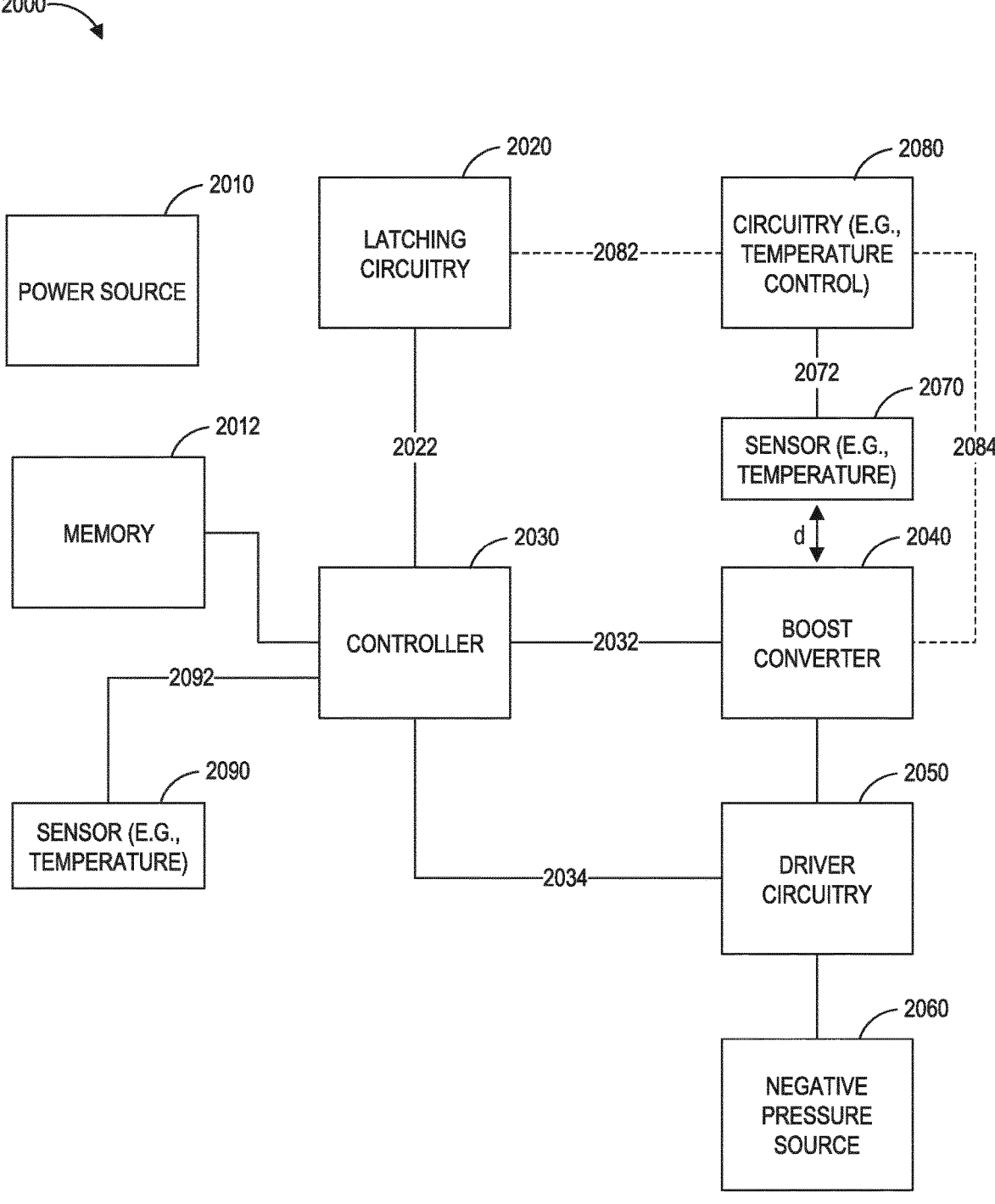
FIG. 9 illustrates a block diagram of the electronics of a TNP system.

FIG. 9 illustrates a block diagram of the electronics 2000 of a TNP system (which can be any of the TNP systems described herein). The electronics (or electronics compo- nents) can include a power source 2010, latching circuitry 2020, a controller 2030 (which can be programmable), a memory 2012, a boost converter (or regulator) 2040 (some- times referred to as boost converter circuitry or boost regulator circuitry), driver circuitry 2050, and a negative pressure source 2060. The negative pressure source 2060 can include a piezoelectric pump (such as, a pump operated by a piezoelectric actuator or transducer). In some cases, the driver circuity 2050 can include H-bridge circuitry. The power source 2010 may include one or more batteries (such as, two 3V batteries). The power source 2010 may provide power to the other electronics components.

Latching circuitry 2020 can include one or more active components (such as, transistors) that activate any one or more of the other components illustrated in FIG. 9 respon- sive to activation of the TNP device, such as removal of the pull tab. Activation can cause the latching circuitry 2020 to facilitate provision of power from the power source 2010 to one or more of the other components, such as to the controller 2030. In some cases, the latching circuitry 2020, responsive to activation, can provide an indication or signal 2022 to the controller 2030. The latching circuitry 2020 can transition from an inactive state (which can be a default state) to an active state responsive to the activation. Respon- sive to receiving the signal 2022, the controller 2030 can operate the negative pressure source 2060. For example, the controller can operate the boost converter 2040 via a signal 2032 (such as, a reference voltage or current) and the driver circuitry 2050 via a signal 2034 (such, as a pulse width modulation signal). Further details of operation of the latching circuitry are described in International Application No. PCT/EP2018/079745, filed Oct. 30, 2018, titled "SAFE OPERTATION OF INTEGRATED NEGATIVE PRES- SURE WOUND TREATMENT APPARATUSES," which is incorporated by reference in its entirety herein.

Power supplied by the power source 2010 (such as, 3V or less or more, 4V or less or more, 5V or less or more, 6V or less or more, 7V or less or more, 8V or less or more, 9V or less or more, or the like) may need to be increased for powering the negative pressure source 2060. The boost converter 2040 can increase the power provided by the power source 2010 to a power level adequate for powering the negative pressure source 2060. The boost converter 2040 can include electronic circuitry configured to generate a higher level of power (for example, higher voltage of DC power) from a lower input power (for example, battery power). In some cases, the boost converter 2040 can be a switched-mode power supply. The boost converter 2040 can be a DC to DC converter with an output voltage greater than the input or source voltage. The boost converter 2040 can increase or step up the power level of the power source 2010 to a power level for operating the negative pressure source 2060. For example, the power source 2010 may provide 6V DC power (or less or more) and the negative pressure source 2060 can require DC power between 30V (or less or more) and 22V (or less or more).

The negative pressure source 2060 can be controlled by alternating periods of activation and deactivation of the negative pressure source. A duty cycle of the negative pressure source 2060 can reflect a portion of time during which the negative pressure source is active relative to a given time interval (such as, 1 second, 5 seconds, 10 seconds, 20 seconds, 30 seconds, etc.). For example, if the negative pressure source 2060 is active for 15 seconds over a 30 second time interval, the duty cycle is 50%. In some cases, increase in the duty cycle of the negative pressure source 2060 can be indicative or a presence of one or more leaks (for example, in the seal between the dressing and the patient). This may be due to the negative pressure source 2060 being active longer in order to establish or maintain a negative pressure set point in presence of one or more leaks. Further details of operation of the boost converter and operation of the negative pressure source are described in International Application No. PCT/EP2020/064601, filed Apr. 26, 2020, titled "SYSTEMS AND METHODS FOR EXTENDING OPERATIONAL TIME OF NEGATIVE PRESSURE WOUND TREATMENT APPARATUSES," which is incorporated by reference in its entirety herein.

Figure 10A:
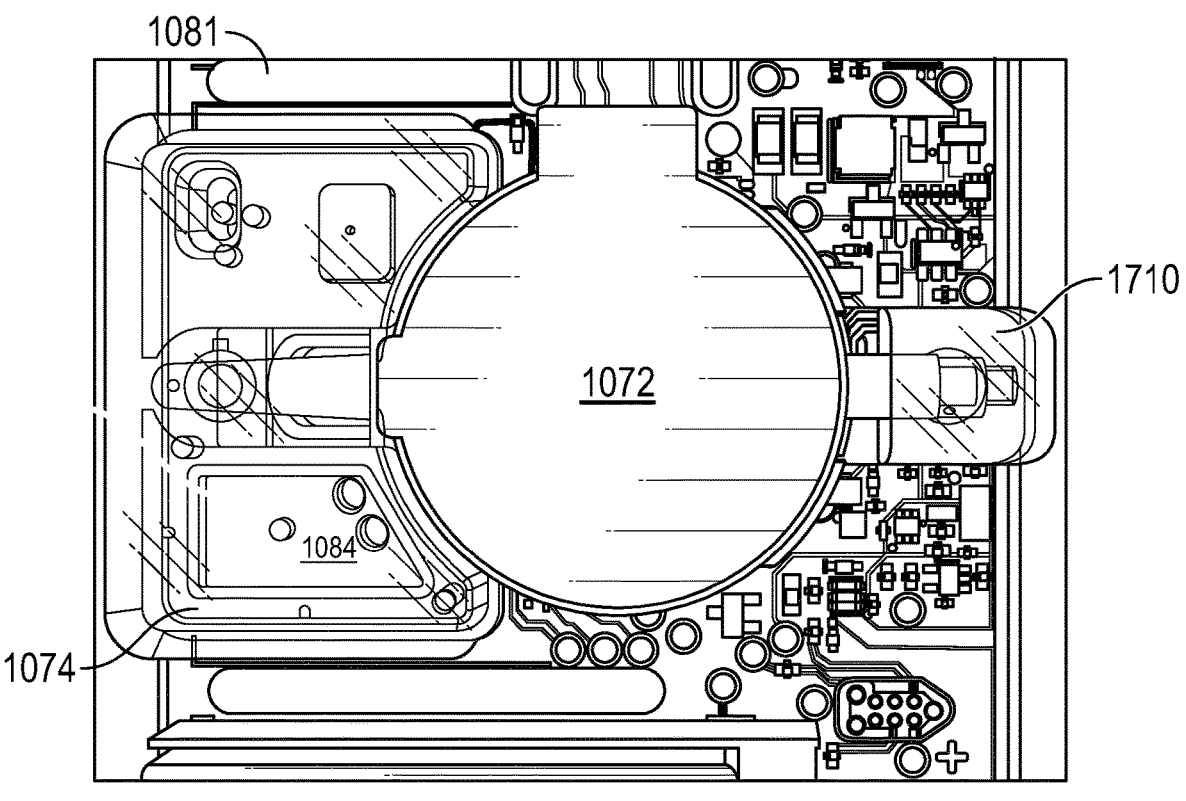
FIGS. 10A-10B illustrate electronics and other components of a TNP system.

One or more electronic components of the TNP system can be positioned on the top side of the system (see, for example, FIGS. 5A, 6A, and 10A). As a result, the top side of the system (facing away from the patient), particularly the portion of the top side where the one or more electronic components are positioned, can be the hottest part of the system during operation. One or more of the components illustrated in FIG. 9 can experience a temperature increase during operation. For example, the temperature of at least one of the boost converter 2040, the driver circuitry 2050, or the negative pressure source 2060 can increase during operation. The negative pressure source 2060 (or the power source 2010 or another component) may be designed to operate safely and effectively at temperatures that are below a maximum temperature threshold (such as, about 40 degrees Celsius or less or more, 41 degrees Celsius or less or more, 42 degrees Celsius or less or more, 48 degrees Celsius or less or more, 50 degrees Celsius or less or more, 60 degrees Celsius or less or more, 70 degrees Celsius or less or more, 80 degrees Celsius or less or more, 90 degrees Celsius or less or more, or the like). Additionally or alternatively, because the electronics can be positioned proximal to the patient (such as, be supported by a wound dressing positioned on the patient's body), increases in the temperature of one or more of the electronics components can cause discomfort or injury (such as, a burn) to the patient. In some cases, increases in the patient's temperature can lead to increases in the temperature of one or more electronics components. To address these problems, the electronics 2000 can monitor the temperature of the one or more of the electronics components. The electronics 2000 can take one or more remedial actions responsive to detecting that the temperature satisfies (for example, meets or exceeds) one or more temperature thresholds. As described herein, the one or more remedial actions can include deactivating one or more electronics components, adjusting operation of one or more electronics components, or the like.

The electronics 2000 can include a sensor 2070 and circuitry 2080 that can perform one or more remedial actions responsive to measurement(s) by the sensor 2070 (and provided to the circuitry 2080 via a signal 2072). The sensor 2070 can be a temperature sensor (for example, a thermistor). In some cases, the sensor 2070 can be positioned proximal to one or more components that can experience increased temperature. For instance, the sensor 2070 can be positioned proximal to the boost converter 2040, which may be an electronics component whose temperature increases the most during operation. As illustrated in FIG. 9, in some cases, the sensor 2070 can be positioned at a distance of no more than "d" from the boost converter 2040. In some instances, the sensor 2070 can be positioned about 4 mm away from the boost converter 2040. In certain implementations, the distance between the sensor 2070 and the boost converter 2040 can be smaller or larger than about 4 mm. A thermal pathway (such as, a conductive trace) can connect the sensor 2070 to the boost converter 2040. One or more of such positioning of the sensor 2070 or presence of the thermal pathway can improve monitoring of the temperature by the sensor 2070.

The circuitry 2080 can include a comparator or the like (further described in connection with FIG. 11) configured to provide an indication responsive to temperature measured by the sensor 2070 satisfying (such as, meeting or exceeding) the maximum temperature threshold (sometimes referred to as over-temperature detection). The indication can cause provision of one or more remedial actions, such as deactivating the negative pressure source 2060 (as illustrated in FIG. 9 by a signal 2084, which can deactivate the boost converter 2040). For example, the circuitry 2080 can include a switch (for example, a transistor) or the like that is activated (or deactivated) responsive to the comparator providing the indication. Activation (or deactivation) of the switch can cause, as illustrated in FIG. 9 by a signal 2082, the latching circuitry 2020 to cease provision of the signal 2022 to the controller 2030. For instance, the latching circuitry can transition from the active state to the inactive state responsive to the activation (or deactivation) of the switch. Responsive to no longer receiving the signal 2022, the controller 2030 can cause a deactivation of the negative pressure source 2060 (such as, by ceasing to provide one or more of the signals 2032 or 2034 or by modifying any of these signals). In some cases, the circuitry 2080 does not include a programmable processor or controller.

Any of the deactivations of the negative pressure source responsive to satisfying the maximum temperature threshold described herein can additionally or alternatively include deactivating a switch (such as, the switch 265) configured to permit a user to control provision of negative pressure wound therapy. Deactivation of such switch can be performed by the controller 2030. In some cases, multiple comparators can be present to facilitate detection for multiple temperature thresholds.

The controller 2030 can independently (or, in some cases, additionally to the circuitry 2080) perform one or more remedial actions responsive to the temperature. A sensor 2090 can sense or monitor temperature of one or more of the one or more electronics components and/or of the patient. The sensor 2090 can provide measurements to the controller 2030 via a signal 2092. As described herein, the controller can perform one or more remedial actions based on comparing sensed temperature to one or more temperature thresholds. For example, the controller 2030 can cause a deactivation of the negative pressure source 2060 (such as, by ceasing to provide one or more of the signals 2032 or 2034 or by modifying any of these signals) responsive to a determination that the sensed temperature satisfies the maximum temperature threshold. Including an independent and redundant mechanism for responding to temperature increases can be advantageous for ensuring safe and effective provision of negative pressure wound therapy to the patient.

Figure 10B:
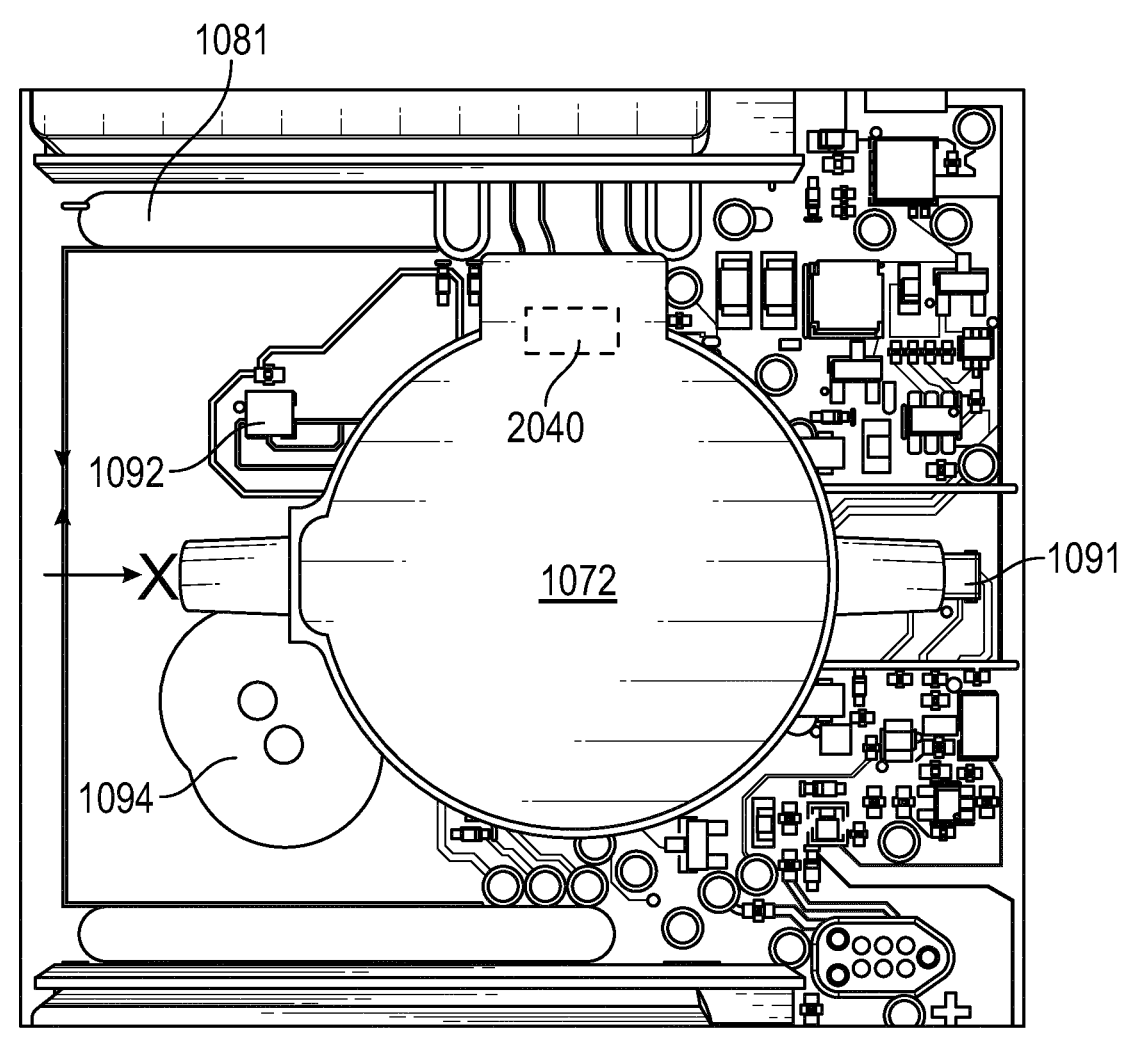

The sensor 2090 can include a plurality of sensors, such as the pressure sensors 1091 and 1092, which can monitor pressure and temperature. As described herein and further with reference to FIGS. 10A-10B, which illustrate electronics and other components 2100 of a TNP system, the pressure sensor 1091 can be positioned to measure pressure of incoming fluid being aspirated by the negative pressure source 2060. For example, the pressure sensor 1091 can be positioned in or proximal to the inlet (for instance, shown as 1710 in FIG. 10A) of the negative pressure source (for instance, designated as 1072 in FIGS. 10A-10B). The pressure sensor 1091 can measure the internal temperature of the TNP system. As described herein, the pressure sensor 1092 can be positioned to measure pressure of the surrounding environment. The pressure sensor 1092 can measure the external temperature. As described herein and further with reference to FIGS. 10A-10B, the pressure sensor 1092 can be positioned in or proximal to the exhaust (for instance, shown as 1074 in FIG. 10A) of the negative pressure source, and as such in fluid communication with the surrounding environment. To facilitate communication with the surrounding environment, there can be one or more vents 1084 in the exhaust mechanism 1074, as shown in FIG. 10A. Additionally, there can be or more vents 1094 in the circuit board 1081, as shown in FIG. 10B.

Due to its positioning, the pressure sensor 1091 can monitor temperature of the patient (for instance, by monitoring the temperature of the dressing). For instance, the pressure sensor 1091 can monitor temperature of fluid aspirated from the wound of the patient (for example, as the fluid enters the inlet of the negative pressure source), which can be indicative of the temperature of the patient. Additionally or alternatively, the pressure sensor 1091 can monitor temperature of at least some of the electronics components, including at least one of the boost converter 2040, the driver circuitry 2050, or the negative pressure source 2060 (whose temperature may increase during operation). Due to its positioning proximal to the negative pressure source (see FIGS. 10A-10B), the pressure sensor 1092 can monitor temperature of at least some of the electronic components. Temperature monitored by the pressure sensor 1092 may reflect contributions from at least one of the boost converter 2040, the driver circuitry 2050, or the negative pressure source 2060. As shown in FIG. 10B, in which the enclosures of the inlet and exhaust mechanisms have been removed, pressure sensor 1092 is positioned proximal to the boost converter 2040 (which can be positioned on the circuit board 1081 in the region indicated by the reference number 2040 under the cover of the negative pressure source 1072). Because the pressure sensor 1092 is positioned in the fluid flow path of fluid aspirated from the wound, the pressure sensor 1092 can additionally monitor temperature contributions due to the patient.

A difference in the temperature monitored by the pressure sensor 1092 and the temperature monitored by the pressure sensor 1091 can reflect temperature of one or more electronics components, such as at least one of the boost converter 2040, the driver circuitry 2050, or the negative pressure source 2060. This can be due to the pressure sensor 1091 monitoring the temperature of the patient and the pressure sensor 1092 monitoring the temperature of the one or more electronics components and the patient. The controller 2030 can compare the temperature difference to one or more thresholds and take one or more remedial actions. As described herein, the controller 2030 can compare the temperature difference to the maximum temperature threshold and, responsive to a determination that the temperature difference satisfies the maximum temperature threshold, cause a deactivation of the negative pressure source 2060.

Additionally or alternatively, the controller 2030 can cause one or more modifications in the operation the negative pressure source 2060 responsive to the temperature difference not satisfying the maximum temperature threshold, but satisfying another one or more thresholds. For example, one or more of the operational time or operational intensity (individually or collectively sometimes referred to as activity) of the negative pressure source 2060 can be adjusted. For example, the activity of the negative pressure source 2060 can be reduced responsive to detection of increasing temperature. In some cases, the maximum temperature threshold can be set at 40 degrees Celsius, 41 degrees Celsius, or 42 degrees Celsius.

A second temperature threshold, which may be indicative of a lower temperature than the maximum temperature threshold, can be used to reduce one or more of the operational time or operational intensity of the negative pressure source 2060 responsive to a detected increase in the temperature. For instance, the second temperature threshold can be set at 35 degrees Celsius (or less or more). The controller 2030 can lower the duty cycle of the negative pressure source 2060 responsive to the temperature difference satisfying the second threshold (but not satisfying the maximum temperature threshold). Additionally or alternatively, the intensity of operation of the negative pressure source 2060 can be reduced (for example, the negative pressure level or set point provided by the negative pressure source can be lowered). Additionally or alternatively, the controller 2030 can deactivate the negative pressure source 2060 for a period of time. Temperature increase may be due to presence of one or more leaks, which can cause the negative pressure source 2060 to operate more often and/or at a higher level of intensity to overcome losses of negative pressure due to the one or more leaks. The adjustment(s) to the operation of the negative pressure source 2060 can facilitate lowering the temperature of one or more of the electronics components. In some cases, one or more additional temperature thresholds can be utilized to further adjust operation of the negative pressure source 2060 responsive to the rising temperature. Such control of the operation of the negative pressure source 2060 responsive to the rising temperature advantageously can, among other things, improve patient comfort, improve safety, and conserve the capacity of the power source 2010 (for instance, by not depleting the power source in attempting to overcome losses of negative pressure due to the one or more leaks).

Additionally or alternatively, the controller 2030 can perform one or more remedial actions responsive to the temperature measured by the pressure sensor 1091. As described herein, the pressure sensor 1091 can monitor temperature of the patient. To promote patient safety and comfort, the controller 2030 can deactivate (such as, permanently or temporarily) the negative pressure source 2060 responsive to temperature measured by the pressure sensor 1091 satisfying a first temperature threshold indicative of high patient temperature. For example, the first temperature threshold can correspond to the patient temperature of 37.5 degrees Celsius (or less or more). For example, the first temperature threshold can be the same as the maximum temperature threshold (such as, 41 degrees Celsius). The controller 2030 can perform such one or more remedial actions in order to not cause further discomfort or injury to the patient due to the temperature increase of the one or more electronics components during provision of negative pressure wound therapy further raising the temperature of the patient. Additionally or alternatively, the controller 2030 can reduce one or more of the operational time or operational intensity of the negative pressure source 2060 responsive to a detected increase in the temperature monitored by the pressure sensor 1091. This can be performed using any of the approaches described above, such as by lowering the duty cycle of the negative pressure source 2060 responsive to satisfying a second temperature threshold. The second temperature threshold can correspond to a lower temperature than the first temperature threshold. For example, the second temperature threshold can be 40 degrees Celsius (or less or more). In some cases, the temperature measured by the pressure sensor 1091 may not be identical to the patient temperature since the flow of aspirated fluid can be cooler than the patient temperature and/or can cool off the pressure sensor 1091). Still, the temperature measured by the pressure sensor 1091 can be indicative of the patient temperature, such that temperature increases sensed by the pressure sensor 1091 can be indicative of temperature increases of the patient.

In some cases, hysteresis can be implemented for controlling the negative pressure source 2060 responsive to the rising temperature. For example, a delay for taking one or more remedial actions could be implemented responsive to determining that the maximum temperature threshold (or the second temperature threshold or any other temperature threshold) has been satisfied. This can prevent adjusting provision of negative pressure wound therapy responsive to one or more errant temperature detections or determinations.

One or more determinations that one or more temperature thresholds has been satisfied can be recorded by the electronics 2000 (such as, saved in the memory 2012). Advantageously, this can help to comply with the IEC 60601-1 standard for safe and effective operation of medical devices or another applicable standard. For example, the controller 2030 can store the one or more determinations in the memory 2012. The controller 2030 can separately store in the memory 2012 the detection of over-temperature by the circuitry 2080 and the detection of over-temperature by the controller 2030. The controller 2030 can additionally separately store in the memory 2012 the determination that the second temperature threshold (or any of the other temperature thresholds) has been satisfied. The controller 2030 can store in the memory temperature detected by one or more of the sensor 2070 or sensor 2090 (such as, by one or more of the sensors 1091 and 1092). This can facilitate debugging the electronics 2000. For example, if it is determined that the sensor 2070 determined that the maximum temperature threshold has been satisfied but the sensor 2090 did not (or vice versa), it may be concluded that one of the sensors (and/or electric connections) may be damaged.

Detection of over-temperature can cause the electronics 2000 to disable the negative pressure source 2060 (such as, temporarily or permanently). In some cases, the electronics 2000 can transition to a non-recoverable error state (or an end of life state), in which the negative pressure source 2060 may be disabled. For example, the controller 2030 can transition to the non-recoverable state (or the end of life state). In the non-recoverable error state (or the end of life state), operation (such as, activation) of the negative pressure source 2060 may be permanently disabled. Further details of disabling operation of the negative pressure source are described in the International Application No. PCT/EP2020/064601, which was published as WO2020/239781 and is incorporated by reference in its entirety herein.

In some cases, the power source 2010 may be depleted responsive to the transition to the non-recoverable error state (or the end of life state). The electronics 2000 can include circuitry (not shown) for depleting the power source 2010. Such circuitry can include one or more resistors connected to the ground. In some cases, depleting the power source 2010 can involve monitoring the temperature and controlling the rate of depletion so as to not cause discomfort or injury (such as, a burn) to the patient. Any of the approaches disclosed herein (such as, using one or more sensors for monitoring temperature of the power source) can be used for monitoring the temperature and controlling the rate of depletion of the power source 2010. In some cases, the power source may be considered to be discharged when its capacity satisfies a capacity threshold. For instance, assuming that the power source 2010 includes one or more lithium 3V batteries, the power source 2010 can be considered to be discharged once the voltage of the one or more batteries reaches 2V or less. Depleting the power source 2010 can be advantageous for patient safety, safe disposal, or the like.

In some variations, one or more components illustrated in FIG. 9 can be omitted or replaced with an alternative component. In some cases, one or more remedial actions described herein can be taken responsive to decreasing temperature, such as the temperature satisfying (for example, meeting or falling below) a minimum temperature threshold and/or any other threshold described herein.

Figure 11:
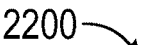
FIG. 11 illustrates a circuit diagram of a portion of a TNP system.

FIG. 11 illustrates a diagram of circuitry 2200 configured to perform over-temperature detection in a TNP system (which can be any of the TNP systems described herein). The circuitry 2200 can at least partially correspond to the circuitry 2080. A temperature sensor 2210 (which can be similar to the sensor 2070) can monitor temperature of one or more components of the TNP system. For example, the temperature sensor 2210 can monitor temperature of the boost converter. The temperature sensor 2210 can be a thermistor. Temperature monitored by the temperature sensor 2210 (which can be output as a voltage signal) can be provided to a comparator 2220 (for instance, as an input 2224). The comparator 2220 can be an operational amplifier. The other input 2222 to the comparator 2220 can correspond to a temperature threshold, such as the maximum temperature threshold. The output 2226 of the comparator 2220 can be indicative of whether the temperature monitored by the temperature sensor 2210 satisfies the temperature threshold. The output 2226 can be used to control a switch 2240, such as a transistor (in which case, the output 2226 can control the gate of the transistor). The output of the switch 2240 can be used to override the output of a latching circuitry (such as, the latching circuitry 2020). In case the temperature monitored by the temperature sensor 2210 satisfies the temperature threshold, the switch 2240 would be turned on. This can cause the output of the latching circuitry to be overridden and the negative pressure source to be deactivated, as described herein. For example, activation of the switch 2240 can cause the output 2202 to be a low voltage (such as, the ground), which can provide an indication to a controller (such as, the controller 2030) to deactivate the negative pressure source. For example, the overriding the output 2202 can be correspond to providing the signal 2084 as described in connection with FIG. 9. In some cases, overriding the output 2202 can cause a boost converter (such as, the boost converter 2040) to be deactivated.

As described herein, the controller can independently perform one or more remedial actions responsive to the temperature. This can be accomplished via a signal 2204, which can correspond to an override signal from the controller. The signal 2204 can correspond to one or more of the signal 2032 provided to the boost converter 2040 or the signal 2034 provided to the driver circuitry 2050, as described in connection with FIG. 9. In some cases, the signal 2204 can be used to control a switch 2250, such as a transistor (in which case, the signal 2204 can control the gate of the transistor). The output of the switch 2250 can be used to override the output of latching circuitry, as described above in connection with the switch 2240.

In some instances, the comparator 2220 may operate incorrectly due to presence of noise in one or more of the inputs 2222 or 2224. For example, noise in the operation of the negative pressure source can affect the ground of the circuitry 2200 (such, as reverberate through the ground plane), which can negatively affect the operation of the comparator 2220. As another example, external noise (such as, environmental noise due to microwave radiation, travelling in a helicopter or plane, travelling in an elevator, or the like) can negatively affect the operation of the comparator 2220. As a result of the presence of noise, the comparator 2220 may not correctly respond to the monitored temperature satisfying (or not satisfying) the temperature threshold (such as, generate the output 2226 at a higher or lower temperature than the temperature threshold). This can compromise patient comfort, safety, or the like.

To address these problems, the circuitry 2200 can include one or more filters 2232 and 2234 at the inputs of the comparator 2220. The filters 2232 and 2234 can be low-pass filters configured to remove high frequency noise (such as, transient spikes). As is illustrated in FIG. 11, the filters 2232 and 2234 can include a resistor and capacitor connected in parallel (or be RC low-pass filters). Additionally or alternatively, a feedback can be created across the comparator 2220. As is illustrated in FIG. 11, a resistor 2238 can be positioned across the non-inverting input 2222 and the output 2226 of the comparator 2220. The resistor 2238 can be referred to as a feedback resistor. The resistor 2238 can introduce hysteresis into the output 2224 of the comparator 2220 (or cause the output 2226 to remain in its current state despite variation in the one or more inputs caused by transient noise).

Approaches for monitoring temperature and taking one or more remedial actions described herein can be generally applicable to any negative pressure wound therapy device configured to be worn by a patient. Safe and effective provision of negative pressure wound therapy can be facilitated. A negative pressure wound therapy device can include electronic components, such as a source of negative pressure and control circuitry. As described herein, there is a risk of causing discomfort or injury (such as, a burn) to the patient as a result of the increased temperature of one of more of the electronic components. It can be advantageous to implement one or more of the described techniques for detecting the rising temperature and taking one or more remedial actions (such as, adjusting or stopping the provision of negative pressure wound therapy. This can be particularly important in cases where the patient is unresponsive or otherwise impaired and, as a result, may not be able to stop the provision of negative pressure wound therapy or remove the negative pressure wound therapy device attached to the patient. Alternatively or additionally, because the negative pressure wound therapy device may be used in different environments, such as in locations where the environmental temperature is high, the described techniques for detecting the rising temperature and taking one or more remedial actions can be advantageous to ensure safe and effective provision of negative pressure wound therapy.

Other Variations

While certain embodiments described herein relate to integrated negative pressure wound therapy systems in which the negative pressure source is supported by the dressing, systems and methods described herein are applicable to any negative pressure wound therapy system or medical system, particularly to systems being positioned on (or worn by) the patient. For example, systems and methods for controlling operation described herein can be used in fluid-proof (such as, water-proof) negative pressure wound therapy systems or medical systems. Such systems can be configured with the negative pressure source and/or electronics being external to the wound dressing, such as with the negative pressure source and/or electronics being positioned in a fluid proof enclosure. Additionally, such systems can be configured to be used within ultrasound delivery devices, negative pressure devices powered by an external power supply, negative pressure devices with a separate pump, and medical devices generally.

Any of the embodiments disclosed herein can be used with one or more features disclosed in U.S. Pat. No. 7,779, 625, titled "DEVICE AND METHOD FOR WOUND THERAPY," issued Aug. 24, 2010; U.S. Pat. No. 7,964,766, titled "WOUND CLEANSING APPARATUS IN SITU," issued on Jun. 21, 2011; U.S. Pat. No. 8,235,955, titled "WOUND TREATMENT APPARATUS AND METHOD," issued on Aug. 7, 2012; U.S. Pat. No. 7,753,894, titled "WOUND CLEANSING APPARATUS WITH STRESS," issued Jul. 13, 2010; U.S. Pat. No. 8,764,732, titled "WOUND DRESSING," issued Jul. 1, 2014; U.S. Pat. No. 8,808,274, titled "WOUND DRESSING," issued Aug. 19, 2014; U.S. Pat. No. 9,061,095, titled "WOUND DRESSING AND METHOD OF USE," issued Jun. 23, 2015; U.S. Pat. No. 10,076,449, issued Sep. 18, 2018, titled "WOUND DRESSING AND METHOD OF TREATMENT"; U.S. patent application Ser. No. 14/418,908, filed Jan. 30, 2015, published as U.S. Publication No. 2015/0190286, published Jul. 9, 2015, titled "WOUND DRESSING AND METHOD OF TREATMENT"; U.S. Pat. No. 10,231,878, titled "TISSUE HEALING," issued Mar. 19, 2019; PCT International Application PCT/GB2012/000587, titled "WOUND DRESSING AND METHOD OF TREATMENT" and filed on Jul. 12, 2012; International Application No. PCT/IB2013/001469, filed May 22, 2013, titled "APPARATUSES AND METHODS FOR NEGATIVE PRESSURE WOUND THERAPY"; PCT International Application No. PCT/IB2013/002102, filed Jul. 31, 2013, titled "WOUND DRESSING AND METHOD OF TREATMENT"; PCT International Application No. PCT/IB2013/002060, filed Jul. 31, 2013, titled "WOUND DRESSING AND METHOD OF TREATMENT"; PCT International Application No. PCT/IB2013/00084, filed Mar. 12, 2013, titled "REDUCED PRESSURE APPARATUS AND METHODS"; International Application No. PCT/EP2016/059329, filed Apr. 26, 2016, titled "REDUCED PRESSURE APPARATUSES"; PCT International Application No. PCT/EP2017/059883, filed Apr. 26, 2017, titled "WOUND DRESSINGS AND METHODS OF USE WITH INTEGRATED NEGATIVE PRESSURE SOURCE HAVING A FLUID INGRESS INHIBITION COMPONENT"; PCT International Application No. PCT/EP2017/055225, filed Mar. 6, 2017, titled "WOUND TREATMENT APPARATUSES AND METHODS WITH NEGATIVE PRESSURE SOURCE INTEGRATED INTO WOUND DRESSING"; PCT International Application No. PCT/EP2018/074694, filed Sep. 13, 2018, titled "NEGATIVE PRESSURE WOUND TREATMENT APPARATUSES AND METHODS WITH INTEGRATED ELECTRONICS"; PCT International Application No. PCT/EP2018/074701, filed Sep. 13, 2018, titled "NEGATIVE PRESSURE WOUND TREATMENT APPARATUSES AND METHODS WITH INTEGRATED ELECTRONICS"; PCT International Application No. PCT/EP2018/079345, filed Oct. 25, 2018, titled "NEGATIVE PRESSURE WOUND TREATMENT APPARATUSES AND METHODS WITH INTEGRATED ELECTRONICS"; PCT International Application No. PCT/EP2018/079745, filed Oct. 30, 2018, titled "SAFE OPERTATION OF INTEGRATED NEGATIVE PRESSURE WOUND TREATMENT APPARATUSES"; each of which is incorporated by reference herein in its entirety.

Although certain embodiments described herein relate to wound dressings, systems and methods disclosed herein are not limited to wound dressings or medical applications. Systems and methods disclosed herein are generally applicable to electronic devices in general, such as electronic devices that can be worn by or applied to a user.

Any value of a threshold, limit, duration, etc. provided herein is not intended to be absolute and, thereby, can be approximate. In addition, any threshold, limit, duration, etc. provided herein can be fixed or varied either automatically or by a user. Furthermore, as is used herein relative terminology such as exceeds, greater than, less than, etc. in relation to a reference value is intended to also encompass being equal to the reference value. For example, exceeding a reference value that is positive can encompass being equal to or greater than the reference value. In addition, as is used herein relative terminology such as exceeds, greater than, less than, etc. in relation to a reference value is intended to also encompass an inverse of the disclosed relationship, such as below, less than, greater than, etc. in relations to the reference value. Moreover, although blocks of the various processes may be described in terms of determining whether a value meets or does not meet a particular threshold, the blocks can be similarly understood, for example, in terms of a value (i) being below or above a threshold or (ii) satisfying or not satisfying a threshold.

Features, materials, characteristics, or groups described in conjunction with a particular aspect, embodiment, or example are to be understood to be applicable to any other aspect, embodiment or example described herein unless incompatible therewith. All of the features disclosed in this specification (including any accompanying claims, abstract and drawings), or all of the steps of any method or process so disclosed, may be combined in any combination, except combinations where at least some of such features or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

While certain embodiments have been described, these embodiments have been presented by way of example only, and are not intended to limit the scope of protection. Indeed, the novel methods and systems described herein may be embodied in a variety of other forms. Furthermore, various omissions, substitutions and changes in the form of the methods and systems described herein may be made. Those skilled in the art will appreciate that in some embodiments, the actual steps taken in the processes illustrated or disclosed may differ from those shown in the figures. Depending on the embodiment, certain of the steps described above may be removed, others may be added. For example, the actual steps or order of steps taken in the disclosed processes may differ from those shown in the figure.

The various components illustrated in the figures or described herein may be implemented as software or firmware on a processor, controller, ASIC, FPGA, or dedicated hardware. Hardware components, such as controllers, processors, ASICs, FPGAs, and the like, can include logic circuitry. The software or firmware can include instructions stored in a non-transitory computer-readable memory. The instructions can be executed by a processor, controller, ASIC, FPGA, or dedicated hardware. Hardware components, such as controllers, processors, ASICs, FPGAs, and the like, can include logic circuitry. Furthermore, the features and attributes of the specific embodiments disclosed above may be combined in different ways to form additional embodiments, all of which fall within the scope of the present disclosure.

Although the present disclosure includes certain embodiments, examples and applications, it will be understood by those skilled in the art that the present disclosure extends beyond the specifically disclosed embodiments to other alternative embodiments or uses and obvious modifications and equivalents thereof, including embodiments which do not provide all of the features and advantages set forth herein. Accordingly, the scope of the present disclosure is not intended to be limited by the specific disclosures of preferred embodiments herein, and may be defined by claims as presented herein or as presented in the future.

Conditional language, such as "can," "could," "might," or "may," unless specifically stated otherwise, or otherwise understood within the context as used, is generally intended to convey that certain embodiments include, while other embodiments do not include, certain features, elements, or steps. Thus, such conditional language is not generally intended to imply that features, elements, or steps are in any way required for one or more embodiments or that one or more embodiments necessarily include logic for deciding, with or without user input or prompting, whether these features, elements, or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. A negative pressure wound therapy system comprising:
a negative pressure source configured to provide negative pressure to a wound of a patient covered by a wound dressing;
a first sensor configured to measure a temperature of at least a first portion of the negative pressure wound therapy system;
a second sensor configured to measure a temperature of at least one of the patient or at least a second portion of the negative pressure wound therapy system;
a non-programmable electronic control circuitry configured to deactivate the negative pressure source responsive to a determination that the temperature measured by the first sensor satisfies a first temperature threshold indicative of unsafe operation, the non-programmable electronic control circuitry comprising an analog comparator configured to output the determination that the temperature measured by the first sensor satisfies the first temperature threshold, and the analog comparator accepting as a first input the temperature measured by the first sensor and as a second input the first temperature threshold; and
a programmable controller configured to control operation of the negative pressure source responsive to temperature measured by the second sensor, the programmable controller configured to control operation of the negative pressure source independently of the non-programmable electronic control circuitry.

2. The system of claim 1, wherein the programmable controller is configured to reduce activity of the negative pressure source responsive to temperature measured by the second sensor satisfying a second temperature threshold that is lower than the first temperature threshold and not satisfying the first temperature threshold.

3. The system of claim 2, wherein reducing activity of the negative pressure source comprises lowering a duty cycle of the negative pressure source.

4. The system of claim 1, further comprising the wound dressing, wherein at least one of the negative pressure source, the first sensor, the second sensor, the non-programmable electronic control circuitry, or the programmable controller is at least partially supported by the wound dressing.

5. The system of claim 1, wherein the temperature measured by the first sensor is indicative of a temperature of the negative pressure source.

6. The system of claim 1, wherein the non-programmable electronic control circuitry is configured to deactivate the negative pressure source responsive to a determination that the temperature measured by the first sensor satisfies the first temperature threshold.

7. The system of claim 1, wherein the analog comparator is configured to operate in a presence of noise as a result of at least one of: one or more inputs of the analog comparator being filtered or a feedback being provided between the first or second input of the analog comparator and an output of the analog comparator.

8. The system of claim 7, wherein the feedback comprises a resistor positioned between a non-inverting input of the analog comparator and the output of the analog comparator.

9. The system of claim 1, further comprising a power source configured to provide power at least to the negative pressure source and a boost converter configured to increase power provided by the power source and provide the increased power to the negative pressure source, and wherein the first sensor is further configured to measure temperature of the boost converter.

10. The system of claim 9, wherein the first sensor is positioned proximal to the boost converter.

11. The system of claim 1, wherein the second sensor comprises a pair of sensors, and wherein the programmable controller is configured to determine a temperature of at least one of the negative pressure source or another component of the negative pressure wound therapy system based on a difference between measurements of first and second sensors of the pair of sensors.

12. The system of claim 11, wherein the first and second sensors of the pair of sensors are configured to measure pressure and temperature.

13. The system of claim 11, wherein the first sensor of the pair of sensors is positioned at an inlet of the negative pressure source and the second sensor of the pair of sensors is positioned at an exhaust of the negative pressure source.

14. The system of claim 1, wherein the programmable controller is configured to control operation of the negative pressure source responsive to temperature measured by the second sensor by at least one of:
deactivating the negative pressure source responsive to the temperature measured by the second sensor satisfying the first temperature threshold;
reducing activity of the negative pressure source responsive to the temperature measured by the second sensor satisfying a second temperature threshold lower than the first temperature threshold and not satisfying the first temperature threshold; or taking no action responsive to the temperature measured by the second sensor not satisfying the second temperature threshold.

15. The system of claim 14, wherein reducing the activity of the negative pressure source comprises reducing a duty cycle of the negative pressure source.

16. The system of claim 1, wherein the programmable controller is further configured to disable activation of the negative pressure source responsive to a determination that the temperature measured by at least one of the first sensor or the second sensor satisfies the first temperature threshold indicative of unsafe operation.

17. The system of claim 1, further comprising a switch configured to permit activation of the negative pressure source, and wherein the switch is configured to be deactivated responsive to a determination that the temperature measured by at least one of the first sensor or the second sensor satisfies the first temperature threshold.

18. The system of claim 1, wherein the second sensor is configured to measure temperature of the patient, and wherein the programmable controller is configured to deactivate the negative pressure source responsive to a determination that the temperature measured by the second sensor satisfies a second temperature threshold indicative of high patient temperature.

19. The system of claim 1, wherein the programmable controller is configured to execute instructions to control operation of the negative pressure source responsive to temperature measured by the second sensor.

20. The system of claim 1, wherein the non-programmable electronic control circuitry comprises only analog circuitry configured solely to allow or disallow provision of negative pressure to the wound.

21. The system of claim 1, wherein the programmable controller is further configured to determine that the first sensor or the second sensor is malfunctioning based on a determination that output of one of the first sensor or second sensor but not the other indicates that the first temperature threshold has been satisfied.

* * * * *